(12) United States Patent
Moellering et al.

(10) Patent No.: US 12,138,320 B2
(45) Date of Patent: Nov. 12, 2024

(54) COMPOSITION AND METHODS FOR TUMOR IMAGING AND TREATMENT

(71) Applicant: The University of Chicago, Chicago, IL (US)

(72) Inventors: Raymond E. Moellering, Chicago, IL (US); Jae Won Chang, Atlanta, GA (US)

(73) Assignee: The University of Chicago, Chicago, IL (US)

( * ) Notice: Subject to any disclaimer, the term of this patent is extended or adjusted under 35 U.S.C. 154(b) by 188 days.

(21) Appl. No.: 17/317,529

(22) Filed: May 11, 2021

(65) Prior Publication Data

US 2021/0346525 A1 Nov. 11, 2021

Related U.S. Application Data

(60) Provisional application No. 63/022,902, filed on May 11, 2020.

(51) Int. Cl.
*A61K 51/04* (2006.01)
*A61P 35/00* (2006.01)
*C07C 271/48* (2006.01)

(52) U.S. Cl.
CPC .............. *A61K 51/04* (2013.01); *A61P 35/00* (2018.01); *C07C 271/48* (2013.01); *C07B 2200/05* (2013.01)

(58) Field of Classification Search
CPC ....... A61K 51/04; A61P 35/00; C07C 271/48; C07B 2200/05
USPC ...................................................... 424/1.85
See application file for complete search history.

(56) References Cited

U.S. PATENT DOCUMENTS

2013/0309170 A1* 11/2013 Reiner ................ A61K 49/0021
424/1.89
2016/0303135 A1* 10/2016 Keilhack ................ A61K 31/69

FOREIGN PATENT DOCUMENTS

WO  WO-2012058115 A2 *  5/2012  ........... C07C 271/44

OTHER PUBLICATIONS

Kniess et al. Med. Chem. Commun. 2015, 6, 1714-1754. (Year: 2015).*
Blum et al. (2005) "Dynamic imaging of protease activity with fluorescently quenched activity-based probes," Nat. Chem. Biol., vol. 1, No. 4, pp. 203-209.
Chang et al. (2011) "A potent and selective inhibitor of KIAA1363/AADACL1 that impairs prostate cancer pathogenesis," Chem. Biol., vol. 18, No. 4, pp. 476-484.
Chang et al. (2012) "An activity-based imaging probe for the integral membrane hydrolase KIAA1363," Angew. Chem. Int. Ed. Engl., vol. 51, No. 4, pp. 966-970.
Chang et al. (2013) "Proteome-wide reactivity profiling identifies diverse carbamate chemotypes tuned for serine hydrolase inhibition," ACS Chem. Biol., vol. 8, pp. 1590-1599.
Chiang et al. (2006) "An enzyme that regulates ether lipid signaling pathways in cancer annotated by multidimensional profiling," Chem. Biol., vol. 13, No. 10, pp. 1041-1050.
Chen et al. (2019) "Design, Synthesis, and Evaluation of 18F-Labeled Monoacylglycerol Lipase Inhibitors as Novel Positron Emission Tomography Probes," J. Med. Chem., vol. 62, No. 19, pp. 8866-8872.
Jessani et al. (2002) "Enzyme activity profiles of the secreted and membrane proteome that depict cancer cell invasiveness," Proc. Natl. Acad. Sci. USA, vol. 99, No. 16, pp. 10335-10340.
Jessani et al. (2005) "A streamlined platform for high-content functional proteomics of primary human specimens," Nat. Methods, vol. 2, No. 9, pp. 691-697.
Kim et al. (2016) "[18F]CFA as a clinically translatable probe for PET imaging of deoxycytidine kinase activity," Proc. Natl. Acad. Sci. USA, vol. 113, No. 15, pp. 4027-4032.
Lanning et al. (2014) "A road map to evaluate the proteome-wide selectivity of covalent kinase inhibitors," Nat. Chem. Biol., vol. 10, No. 9, pp. 760-767.
Lentz et al. (2018) "Identification of a S. aureus virulence factor by activity-based protein profiling (ABPP)," Nat. Chem. Biol., vol. 14, No. 6, pp. 609-617.
Li et al. (2017) "An activity-dependent proximity ligation platform for spatially resolved quantification of active enzymes in single cells," Nat. Commun., vol. 8, 1775.
Li et al. (2019) "Ultrasensitive, multiplexed chemoproteomic profiling with soluble activity-dependent proximity ligation," Proc. Natl. Acad. Sci. USA, vol. 116, No. 43, pp. 21493-21500.
Liu et al. (1999) "Activity-based protein profiling: the serine hydrolases," Proc. Natl. Acad. Sci. USA, vol. 96, No. 26, pp. 14694-14699.
Marcus et al. (2014) "Brain PET in the diagnosis of Alzheimer's disease," Clin. Nucl. Med., vol. 39, No. 10, pp. e413-e422.

(Continued)

*Primary Examiner* — Michael G. Hartley
*Assistant Examiner* — Sean R Donohue
(74) *Attorney, Agent, or Firm* — Jenkins, Taylor & Hunt, P.A.

(57) ABSTRACT

Radioisotope-labeled small molecule activity-based probes that target the cancer associated serine hydrolase neutral cholesterol ester hydrolase 1 (NCEH1) are described. The probes can undergo a reaction with the NCEH1, resulting in covalent bonding of a portion of the probe molecule to the NCEH1. Also described are methods of labeling NCEH1 in biological samples, such as cells or tissue, and methods of visualizing tumors using the radioisotope-labeled NCEH1 probes as tracer compounds, either alone or in combination with assessing the efficacy of a cancer treatment or potential cancer treatment.

11 Claims, 18 Drawing Sheets
(12 of 18 Drawing Sheet(s) Filed in Color)
Specification includes a Sequence Listing.

(56) References Cited

OTHER PUBLICATIONS

Moellering et al. (2012) "How chemoproteomics can enable drug discovery and development," Chem. Biol., vol. 19, No. 1, pp. 11-22.

Muir et al. (2019) "Measuring Dynamic Changes in the Labile Iron Pool in Vivo with a Reactivity-Based Probe for Positron Emission Tomography," ACS Cent. Sci., vol. 5, No. 4, pp. 727-736.

Nomura et al. (2010) "Activity-based protein profiling for biochemical pathway discovery in cancer," Nat. Rev. Cancer, vol. 10, No. 9, pp. 630-638.

Okazaki et al. (2008) "Identification of neutral cholesterol ester hydrolase, a key enzyme removing cholesterol from macrophages," J. Biol. Chem., vol. 283, No. 48, pp. 33357-33364.

Rashidian et al. (2015) "Noninvasive imaging of immune responses," Proc. Natl. Acad. Sci. USA, vol. 112, No. 19, pp. 6146-6151.

Sanman et al. (2014) "Activity-based profiling of proteases," Annu. Rev. Biochem., vol. 83, pp. 249-273.

Witney et al. (2015) "PET imaging of tumor glycolysis downstream of hexokinase through noninvasive measurement of pyruvate kinase M2," Sci. Transl. Med., vol. 7, Article 310ra169.

Betts et al. (2016) "Synthesis, in Vitro Evaluation, and Radiolabeling of Fluorinated Puromycin Analogues: Potential Candidates for PET Imaging of Protein Synthesis," J. Med. Chem., vol. 59, No. 20, pp. 9422-9430.

Chang et al. (2020) "In Vivo Imaging of the Tumor-Associated Enzyme NCEH1 with a Covalent PET Probe," Angew. Chem. Int. Ed., vol. 59, pp. 15161-15165.

Chang et al. (2020) "In Vivo Imaging of the Tumor-Associated Enzyme NCEH1 with a Covalent PET Probe (Supporting Information)," Angew. Chem. Int. Ed., pp. 1-12.

Li et al. (2019) "A Concise, Modular Antibody—Oligonucleotide Conjugation Strategy Based on Disuccinimidyl Ester Activation Chemistry," ChemBioChem, vol. 20, Issue 12, pp. 1599-1605.

Shults et al. (2003) "Versatile Fluorescence Probes of Protein Kinase Activity," J. Am. Chem. Soc., vol. 125, No. 47, pp. 14248-14249.

* cited by examiner

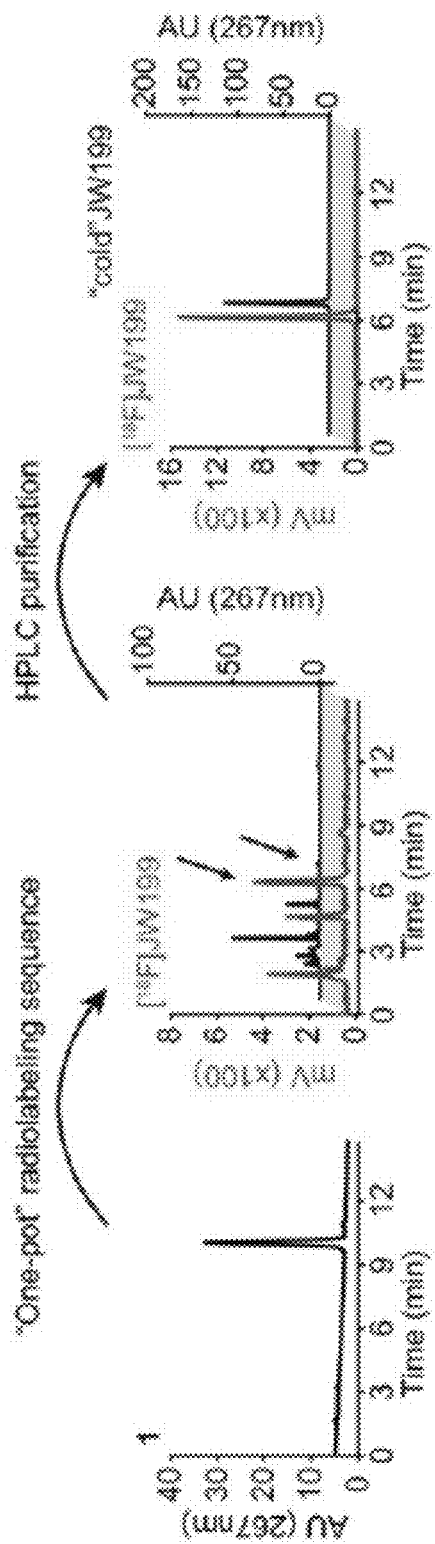
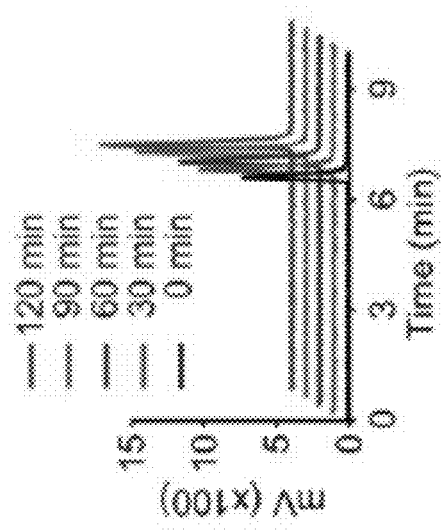
FIG. 1E
FIG. 1F

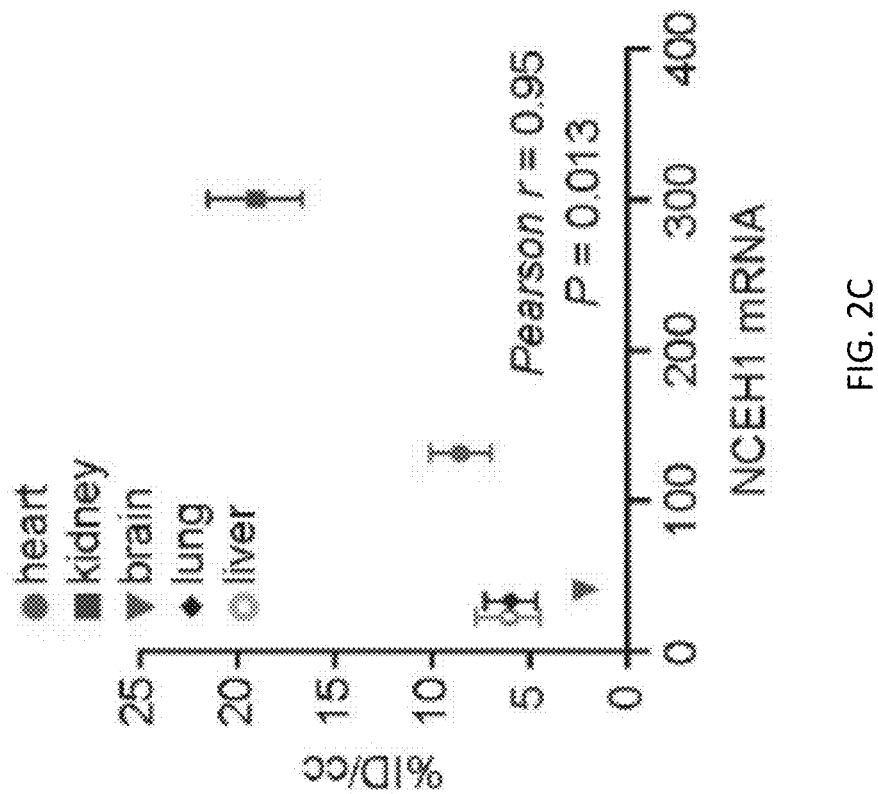
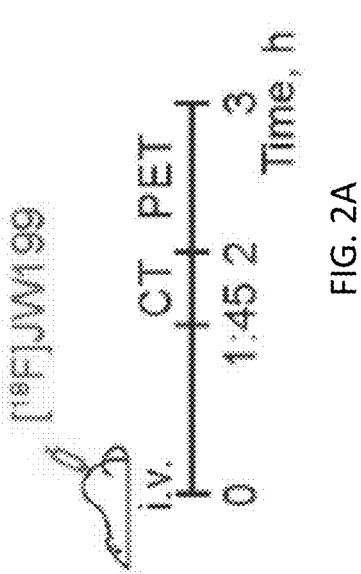
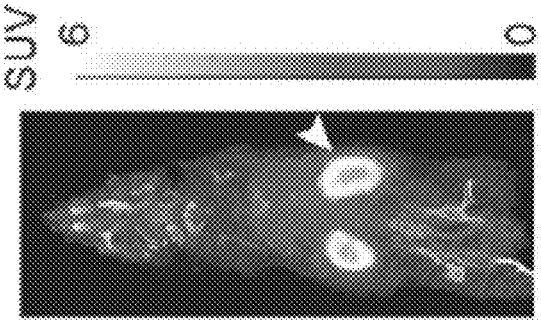
FIG. 2A
FIG. 2B
FIG. 2C

COMPOSITION AND METHODS FOR TUMOR IMAGING AND TREATMENT

RELATED APPLICATIONS

The presently disclosed subject matter claims the benefit of U.S. Provisional Patent Application Ser. No. 63/022,902, filed May 11, 2020, the disclosure of which is incorporated herein by reference in its entirety.

REFERENCE TO SEQUENCE LISTING SUBMITTED ELECTRONICALLY

The content of the electronically submitted sequence listing in ASCII text file (Name: 3072-18-2.ST25.txt; Size: 2 kilobytes; and Date of Creation: May 11, 2021) filed with the application is incorporated herein by reference in its entirety.

TECHNICAL FIELD

The presently disclosed subject matter provides compositions and methods for the in vivo imaging of tumors. More particularly, the presently disclosed subject matter relates to radioisotope-substituted activity-based probes that label active neutral cholesterol ester hydrolase 1 (NCEH1).

BACKGROUND

Activity-based probes and profiling methods can provide for interrogation of the active proteome in a wide range of biological contexts.[1-3] In general, chemical probes can be applied to cell lysates or intact cells, followed by detection and quantification of active enzymes by gel separation, mass spectrometry, or activity-dependent proximity ligation.[4-6] To detect and visualize specific enzyme targets in live cells, target-selective, activity-based fluorescent probes targeting proteases, metabolic hydrolases, and kinases in mammalian and prokaryotic cell have been developed.[7-10] Most fluorescent probes, however, lack the pharmacologic and optical properties necessary for in vivo imaging applications. Instead, radiolabeled small molecules have been deployed for whole-body imaging of global molecular and physiologic processes.[11,12] For example, the radiotracer [$^{18}$F]fluorodeoxyglucose (FDG) is widely used for positron emission tomography (PET) imaging of glucose-avid tumor cells in vivo.[12]

Radiotracers that detect nutrient uptake, disease-associated protein conformation and abundance (e.g., As aggregates in Alzheimer's disease), cell surface markers, metals and other molecular features have been developed with the intention of clinical deployment.[13-16] However, despite the longstanding use of PET in the clinic, there remains a dearth of highly specific molecular probes to report disease-associated molecular activities. Therefore, there is an urgent need to identify new disease-associated biologic targets and new types of coupled molecular probes for diagnostic imaging purposes.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In some embodiments, the presently disclosed subject matter provides a compound having a structure of the formula:

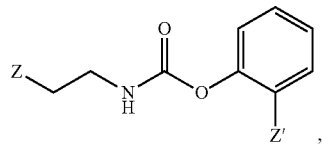

wherein: Z' is selected from alkyl, cycloalkyl, heterocyclic, aryl, heteroaryl; and Z is selected from —Ar$_1$—O-L-R and —NH—C(=O)—Ar$_2$—O-L-R, wherein Ar$_1$ and Ar$_2$ are each selected from aryl, heteroaryl, heterocyclic, substituted aryl, substituted heteroaryl, and substituted heterocyclic; L is alkylene; and R is a halogen radioisotope. In some embodiments, R is selected from the group comprising $^{18}$F, $^{38}$Cl, $^{75}$Br, $^{78}$Br, $^{77}$Br, $^{82}$Br, $^{123}$I, $^{124}$I, $^{125}$I, $^{131}$I, and $^{211}$At. In some embodiments, R is $^{18}$F.

In some embodiments, the compound has a structure of one of the formulas:

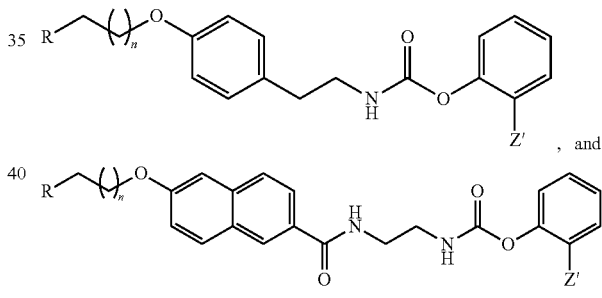

wherein: Z' is selected from alkyl, cycloalkyl, heterocyclic, aryl, and heteroaryl; n is an integer between 0 and 5; and R is a halogen radioisotope. In some embodiments, Z' is isopropyl. In some embodiments, n is 1 or 2. In some embodiments, the compound is selected from the group comprising:

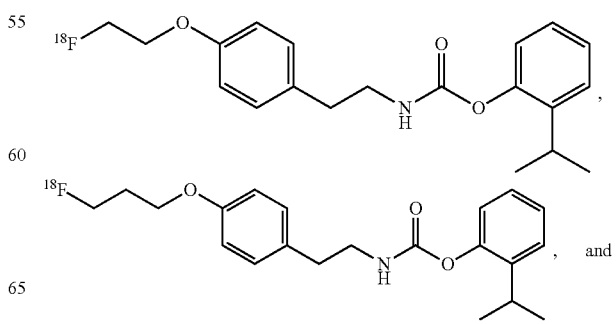

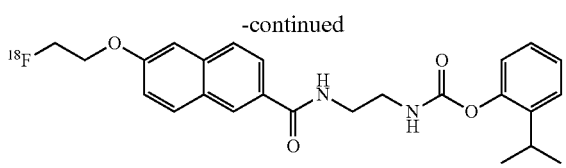

In some embodiments, the presently disclosed subject matter provides a method of labeling neutral cholesterol ester hydrolase 1 (NCEH1), wherein the method comprises contacting a sample with a compound having a structure of the formula:

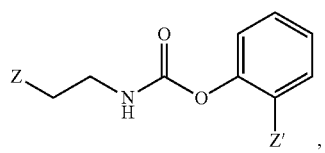

wherein: Z' is selected from alkyl, cycloalkyl, heterocyclic, aryl, heteroaryl; and Z is selected from —Ar$_1$—O-L-R and —NH—C(=O)—Ar$_2$—O-L-R, wherein Ar$_1$ and Ar$_2$ are each selected from aryl, heteroaryl, heterocyclic, substituted aryl, substituted heteroaryl, and substituted heterocyclic; L is alkylene; and R is a halogen radioisotope. In some embodiments, R is $^{18}$F. In some embodiments, the compound is selected from the group comprising:

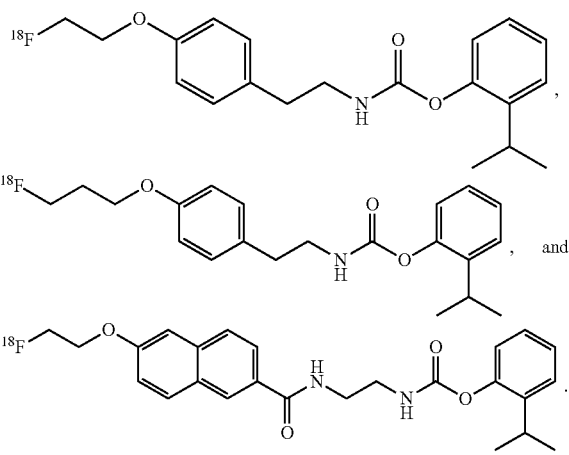

In some embodiments, the sample comprises one of the group comprising a cell, a cell culture, a tissue, an organ, and a subject.

In some embodiments, the presently disclosed subject matter provides a method of visualizing a tumor in a subject, wherein the method comprises: (a) administering to a subject having or suspected of having a tumor a tracer compound having the formula:

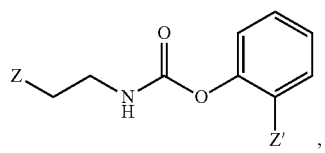

wherein: Z' is selected from alkyl, cycloalkyl, heterocyclic, aryl, heteroaryl; and Z is selected from —Ar$_1$—O-L-R and —NH—C(=O)—Ar$_2$—O-L-R, wherein Ar$_1$ and Ar$_2$ are each selected from aryl, heteroaryl, heterocyclic, substituted aryl, substituted heteroaryl, and substituted heterocyclic; L is alkylene; and R is a halogen radioisotope; and (b) detecting radioactivity of the tracer compound, thereby visualizing a tumor or the edges thereof when a tumor is present in said subject. In some embodiments, R is $^{18}$F. In some embodiments, Z' is isopropyl.

In some embodiments, the tracer compound is selected from:

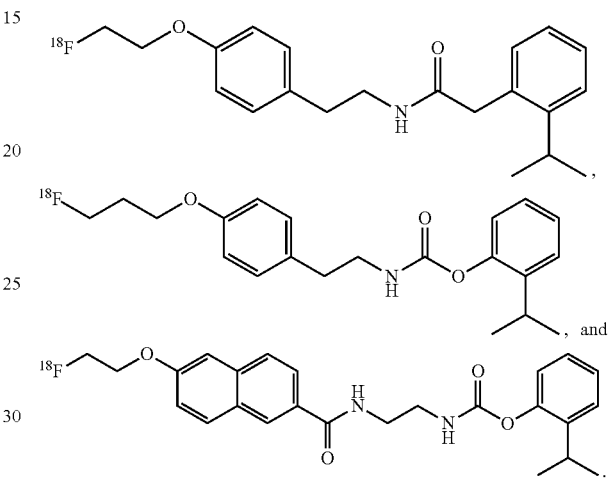

In some embodiments, detecting radioactivity of the tracer compound is performed via single-photon emission computed tomography (SPECT) and/or positron emission tomography (PET).

In some embodiments, the subject has a tumor and the method further comprises: (c) administering a cancer treatment or a potential cancer treatment to the subject; (d) repeating steps (a) and (b), thereby re-visualizing the tumor visualized in step (b); and (e) comparing the tumor as visualized in step (b) to the tumor as visualized in step (d), thereby determining the in vivo effectiveness of the cancer treatment or the potential cancer treatment. In some embodiments, the cancer treatment or potential cancer treatment for cancer is a pharmaceutical agent known or suspected to treat cancer. In some embodiments, comparing the tumor as visualized in step (b) to the tumor as visualized in step (d) comprises comparing the size of the tumor visualized in step (b) to the size of the tumor visualized in step (d).

In some embodiments, when a tumor is present in the subject, the method further comprises administering a cancer treatment to said subject. In some embodiments, the cancer treatment is selected from surgery, radiation, and chemotherapy. In some embodiments, the cancer treatment is administered directly to the visualized tumor.

Accordingly, it is an object of the presently disclosed subject matter to provide radioisotope-labeled compounds and methods of using the compounds to label NCEH1 and to visualize tumors. This and other objects are achieved in whole or in part by the presently disclosed subject matter.

Further, an object of the presently disclosed subject matter having been stated above, other objects and advantages of the presently disclosed subject matter will become apparent to those skilled in the art after a study of the following description, Figures, and Examples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1F: JW199 is a potent and specific inhibitor of neutral cholesterol ester hydrolase 1 (NCEH1). FIG. 1A is a drawing of the chemical structure of an exemplary NCHE1 inhibitor of the presently disclosed subject matter, 2-isopropylphenyl-(4-(2-fluoroethoxy)phenethyl)carbamate, also referred to herein as JW199. FIG. 1B is a photographic image of gel-based activity-based protein profiling (ABPP) of serine hydrolase activity in membrane proteome fractions of MDA-MB231 breast cancer cells treated with the indicated concentrations (0 micromolar (μM) to 50 μM) of JW199 in vitro (left) and in situ (right). Bands represent serine hydrolases labeled with the family-wide fluorescent chemical probe, fluorophosphonate-rhodamine (FP-Rho). Arrowheads indicate bands corresponding to NCEH1 (glycosylated NCEH1 presents with a doublet banding pattern). FIG. 1C is a graph of the dose-dependent inhibition (% inhibition versus log concentration of JW199) of NCEH1 with JW199 in MDA-MB231 breast cancer cells in vitro (red) and in situ (black). Data shown represent the mean and 95% confidence interval (95% C.I.) from n=3 biological replicates. FIGS. 1D-1F show the radiosynthesis and chemical stability of fluorine-18-labeled JW199, i.e., [$^{18}$F]JW199. FIG. 1D is a schematic drawing showing a route for the radiosynthesis of [$^{18}$F]JW199. FIG. 1E is a series of graphs showing absorbance (black) and crude radioactivity (red) chromatograms of pure toluenesulfonate (TsO)-JW199 starting material (1, left), $^{18}$F-labeled, crude JW199 (middle), and HPLC-purified, radiolabeled [$^{18}$F]JW199 (right). Arrowheads indicate peaks corresponding to the [$^{18}$F] JW199 radiosynthetic product. FIG. 1F is a graph showing the stability of [$^{18}$F]JW199 in phosphate buffered saline containing 10% ethanol over time (in minutes (min)), as measured by radioactive high-performance liquid chromatography (HPLC).

FIGS. 2A-2F: Neutral cholesterol ester hydrolase 1 (NCEH1)-dependent imaging with [$^{18}$F]JW199. FIG. 2A is a schematic diagram showing the experimental timeline of in vivo fluorine-18-labeled 2-isopropylphenyl-(4-(2-fluoroethoxy)phenethyl)carbamate (JW199), i.e., [$^{18}$F]JW199, administration and imaging. FIG. 2B is an image of a whole-body positron emission tomography computed tomography (PET-CT) scan of wild-type mice following intravenous (i.v.) administration of about 100 microcurie (μCi) of [$^{18}$F]JW199. The figure shows accumulation of radiosignal in the kidneys, a known distribution site (arrowhead). Image is representative of n=3 mice. FIG. 2C is a graph showing correlation between Nceh1 messenger RNA (mRNA) abundance in various mouse tissues (heart (filled circle), kidney (square), brain (triangle), lung (diamond) and liver (unfilled circle); obtained from BioGPS.org) and [$^{18}$F] JW199 accumulation, quantified as the percentage of injected dose per volume (cubic centimeter (cc)) of bodyweight (% ID/cc). FIG. 2D is a graph of $^{18}$F-JW199 radiosignal kinetics in the indicated organs (heart (filled circle), kidney (square), brain (downward-pointing triangle), bladder (upward pointing triangle), lung (diamond), and liver (unfilled circle)) following radiotracer injection. FIG. 2E is a schematic drawing of the timeline of 2-isopropylphenyl-(2-(naphthalen-2-yl)ethyl)carbamate (JW480) oral administration followed by i.v. [$^{18}$F]JW199 administration (top) and related PET-CT imaging (bottom). [$^{18}$F]JW199 accumulation in the kidneys and heart is visibly decreased in the competitor-treated mouse. Images are representative of n=3 mice per group. FIG. 2F is a graph showing radiotracer signal quantification (percentage of injected dose per volume (% ID/cc) in tissues from mice in the [$^{18}$F]JW199 (red) and JW480+[$^{18}$F]JW199 (blue) treatment groups, 3 hours post injection of [$^{18}$F]JW199. Data shown represent mean±standard deviation from n=3 mice per group. Ns, not significant, *p<0.05, **p<0.01, as determined by Student's t-test.

FIG. 3A is a series of images of a representative whole-body positron emission tomography-computed tomography (PET-CT) scan of a MDA-MB231 breast cancer cell tumor-bearing mouse 3 hours after administration of fluorine-18-labeled JW199, i.e., [$^{18}$F]JW199. Tumor boundary is delineated in the whole-body image and magnified in inset. Image is representative of n=3 mice. FIGS. 3B and 3C are graphs that show neutral cholesterol ester hydrolase 1 (NCEH1) activity profiling in the edge (red, circles) and inside (blue, squares) areas of MDA-MB231 tumor xenografts, as measured via gel-based profiling with 5,5-difluoro-7-(3-((2-(((2-isopropylphenoxy)carbonyl)amino)ethyl)-amino)-3-oxo-propyl-1,3-dimethyl-5H-dipyrrolo[1,2-c:2'1'-f][1,3,2]diazaborinin-4-ium-5-uide (JW576) (FIG. 3B) and soluble activity-dependent proximity ligation (sADPL) profiling (FIG. 3C). FIG. 3D is a graph of glyceraldehyde-3-phosphate dehydrogenase (GAPDH)-normalized NCEH1 protein levels in the edge (red) and inside (blue) areas of tumor xenografts. FIG. 3E is a representative NCEH1 immunofluorescence image of xenograft sections (5 micrometer (μm) thick). Blue signal indicates 4',6-diamindino-2-2phenylindole (DAPI)-stained nuclei, while red signal indicates NCEH1. Division between the edge and inside areas are indicated with a dashed line. Scale bar=5 μm. Data shown represent the mean±standard deviation from n=3 mice (FIGS. 3C and 3E) and triplicate samples from n=3 mice (FIG. 3D). *p<0.001, **p<0.0001 as determined by Student's t-test.

FIG. 5A is a schematic diagram showing the chemical structures of 2-isopropylphenyl-(4-(3-fluoropropoxy)phenethyl)carbamate (JW245) and 2-isopropylphenyl (2-(6-(2-fluoroethoxy)-2-naphthamido)ethyl)carbamate (JW291). FIG. 5B is a photographic image of a gel showing activity-based protein profiling (ABPP) of serine hydrolase activity in the membrane proteome fraction of MDA-MB231 breast cancer cells treated in situ across a range of JW245 (left) and JW291 (right) concentrations (0 micromolar (μM) to 25 μM). Gels are representative n=3 independent experiments.

FIG. 6A is a pair of photographic images of gels showing ABPP of serine hydrolase activity in the soluble proteome fraction of MDA-MB231 breast cancer cells treated with a range of JW199 concentrations (0 micromolar (μM) to 25 μM or 50 μM) in vitro (left) and in situ (right). JW199 does not inhibit the activity of all detected serine hydrolases. FIGS. 6B and 6C are pairs of photographic images of ABPP of serine hydrolase activity in the membrane (FIG. 6B) and soluble (FIG. 6C) proteome fractions of PC3 prostate cancer cells treated with a range of JW199 concentrations (0 micromolar (µM) to 25 µM or 50 µM) in vitro (left image of each pair) and in situ (right image of each pair). Gels are representative n=3 independent experiments. FIG. 6D is a graph showing calculated in vitro (red, dashed line) and in situ (black, solid line) 50% inhibitory concentration (IC50) values for JW199 in PC3 cells.

FIG. 9A is a schematic drawing showing the chemical structure of JW480. FIG. 9B is a composite gel image of the ABPP profiles of the murine membrane proteomes from brain, heart, kidney, lung, liver and spleen following treatment with [$^{18}$F]JW199 with or without JW480.

FIG. 12A is a representative whole-body positron emission tomography-computed tomography (PET-CT) image of a PC3 prostate cancer cell tumor-bearing mouse and tumor boundary image in inset. Image is representative of n=4 mice. B. FIG. 12B is a graph showing the ex vivo biodistribution of [$^{18}$F]JW199 in mice bearing PC3 xenografts. Quantification of radiotracer signal in the indicated tissues 3 hours after injection of 150 microcurie (µCi) of radiotracer. Data are means percentage injected dose per cubic centimeter (% ID/cc)±standard deviation (SD) (n=4 male mice). FIG. 12C is a graph of the glyceraldehyde-3-phosphate dehydrogenase (GAPDH)-normalized neutral cholesterol ester hydrolase 1 (NCEH1) protein levels in the edge (red) and inside (blue) areas of tumor xenografts, ***p<0.001 as determined by Student's t-test. Corresponding gel images are shown above the graph.

DETAILED DESCRIPTION

Figure 1B:
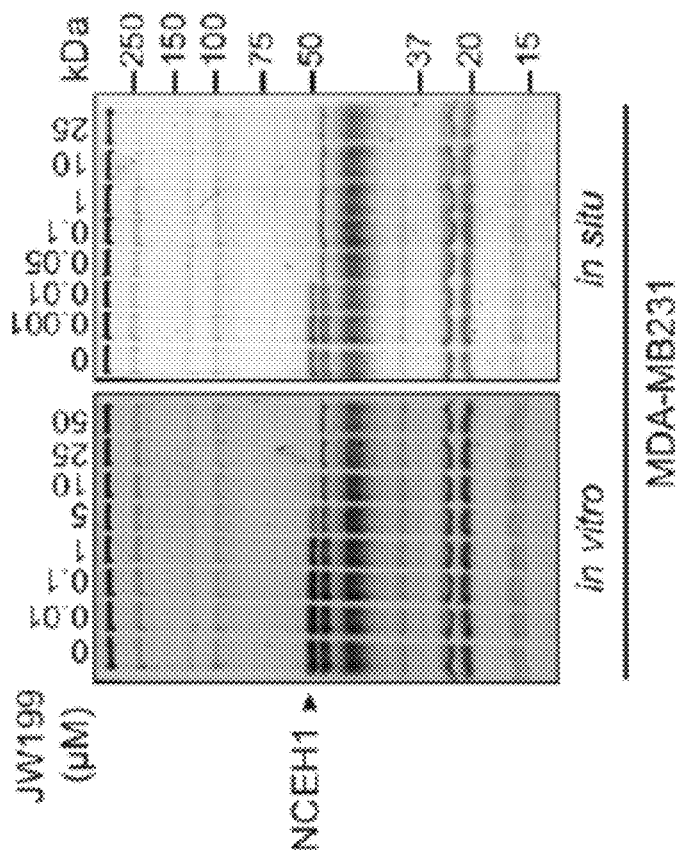
Figure 1A:
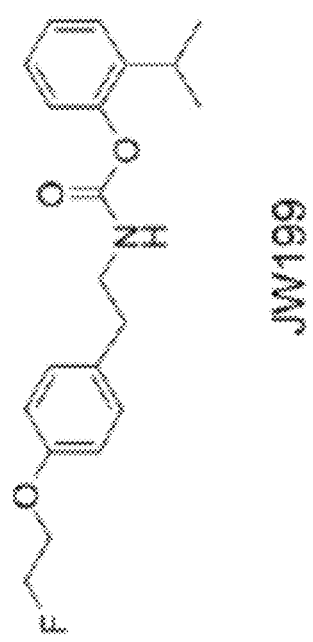
Figure 1C:
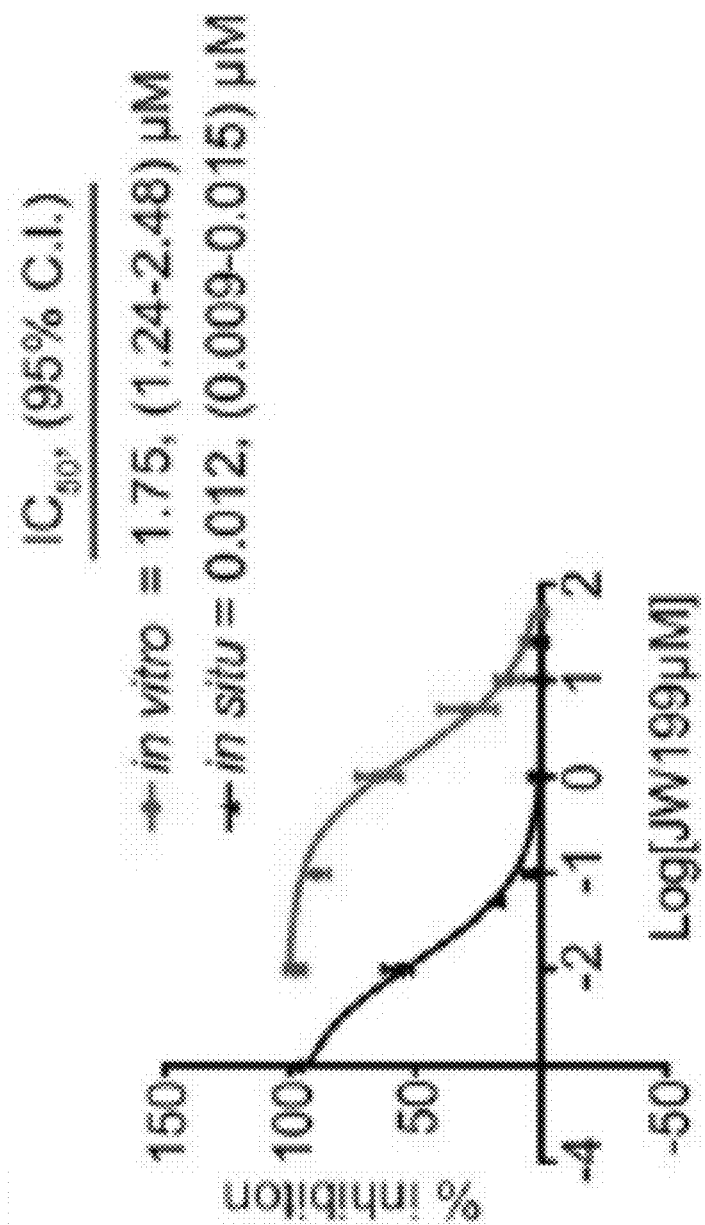

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a," "an," and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "comprising," which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

Unless otherwise indicated, all numbers expressing quantities of size, temperature, time, weight, volume, concentration, capacitance, specific capacity, discharge capacity, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value is meant to encompass variations of in one example ±20% or ±10%, in another example ±5%, in another example ±1%, and in still another example ±0.1% from the specified amount, as such variations are appropriate to perform the disclosed methods.

Numerical ranges recited herein by endpoints include all numbers and fractions subsumed within that range (e.g. 1 to 5 includes, but is not limited to, 1, 1.5, 2, 2.75, 3, 3.90, 4, and 5).

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, naphthyl, anthracenyl, phenanthrenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Cyclic" and "cycloalkyl" refer to a non-aromatic mono- or multicyclic ring system of about 3 to about 10 carbon atoms. The cycloalkyl group can be optionally partially unsaturated. The cycloalkyl group can be also optionally substituted with an alkyl group substituent as defined herein, oxo and/or alkylene. There can be optionally inserted along the cyclic alkyl chain one or more oxygen, sulphur or substituted or unsubstituted nitrogen atoms, wherein the nitrogen substituent is hydrogen, lower alkyl, or aryl, thus providing a heterocyclic group. Representative monocyclic cycloalkyl rings include cyclopropyl, cyclobutyl, cyclopentyl, cyclohexyl and cycloheptyl. Exemplary multicyclic cycloalkyl rings include adamantyl, octahydronaphthyl, decalin, camphor, camphane, and noradamantyl.

The term "heterocyclic" refers to a non-aromatic or aromatic mono- or multicyclic ring system of about 3 to about 12 atoms that comprises at least one heteroatom, e.g., N, O, or S. The group can be saturated, partially unsaturated, or unsaturated. Exemplary heterocyclic groups include, but are not limited to, furanyl, pyrrolyl, pyridinyl, pyranyl, piperidinyl, morpholinyl, dioxanyl, pyrrolidinyl, oxanyl, thiolanyl, and thiophenyl. Heterocyclic groups can be unsubstituted or substituted with one or more alkyl group substituents or aryl group substituents.

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The terms "hydroxyl" and "hydroxy" refer to the —OH group.

The terms "halo", "halide", or "halogen" as used herein refer to fluorine (F), chlorine (Cl), bromine (Br), iodine (I), and astatine (At) and substituent moieties comprising atoms thereof.

The term "carbamate" refers to the group —O—C(=O)—NH— or —O—C(=O)—NR'—, wherein R' is alkyl, substituted alkyl, aralkyl, substituted aralkyl, aryl, or substituted aryl.

By the term "protecting group" is meant a group which inhibits or suppresses undesirable chemical reactions, but which is designed to be sufficiently reactive that it can be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Third Edition, John Wiley & Sons, 1999).

The terms "radioisotope" and "radionuclide" as used herein refer to a radioactive isotope of an element, i.e., an unstable isotope that has excess nuclear energy and that can undergo radioactive decay. In some embodiments, the term "radioisotope" is understood to mean an isotope of natural or artificial origin which demonstrates radioactive properties. In some embodiments, the radioisotope is selected from the group comprising fluorine-18 ($^{18}$F), chlorine-36 ($^{36}$Cl), bromine-75 ($^{75}$Br), bromine-76 ($^{76}$Br), bromine-77 ($^{77}$Br), bromine-82 ($^{82}$Br), iodine-123 ($^{123}$I), iodine-124 ($^{124}$I), iodine-125 ($^{125}$I) iodine-131 ($^{131}$I), astatine-210 ($^{210}$At) or astatine-211 ($^{211}$At).

The terms "tracer", "tracer compound", "radiotracer", "radiotracer compound", "in vivo imaging agent", and the like in the context of the presently disclosed subject matter refer to a radiolabelled compound suitable for in vivo imaging.

The term "in vivo imaging" as used herein refers to those techniques that noninvasively produce images of all or part of the internal aspect of a subject. Examples of in vivo imaging techniques suitable in the context of the presently disclosed subject matter include single-photon emission tomography (SPECT) and positron emission tomography (PET), both of which are well-known techniques in the field of in vivo imaging (see, for example, "Emission Tomography: the Fundamentals of PET and SPECT"; 2004 Academic Press: Wernick and Aarsvold, Eds.).

A "sample," as used herein, typically refers to a biological sample comprising cells or cellular material. In some embodiments, the sample is from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture, e.g., a cell or tissue extract.

The term "tumor" as used herein refers to an abnormal growth of cells, e.g., that forms a mass or lump of tissue. As used herein the term "tumor" typically refers to a cancerous tumor.

The term "cancer" as used herein refers to diseases caused by uncontrolled cell division and/or the ability of cells to metastasize, or to establish new growth in additional sites. The terms "malignant", "malignancy", "neoplasm", "cancer" and variations thereof refer to cancerous cells or groups of cancerous cells.

Particular types of cancer include, but are not limited to, skin cancers (e.g., melanoma), connective tissue cancers (e.g., sarcomas), adipose cancers, breast cancers, head and neck cancers, lung cancers (e.g., mesothelioma), stomach cancers, pancreatic cancers, ovarian cancers, cervical cancers, uterine cancers, anogenital cancers (e.g., testicular cancer), kidney cancers, bladder cancers, colon cancers, prostate cancers, central nervous system (CNS) cancers, retinal cancer, blood, neuroblastomas, multiple myeloma, and lymphoid cancers (e.g., Hodgkin's and non-Hodgkin's lymphomas).

The term "metastatic cancer" refers to cancer that has spread from its initial site (i.e., the primary site) in a patient's body.

The terms "anticancer drug" and "chemotherapeutic" refer to drugs (e.g., natural or synthetic small molecule chemical compounds) or prodrugs known or suspected of being able to treat a cancer (i.e., to kill cancer cells, prohibit proliferation of cancer cells, or treat a symptom related to cancer). Traditional or conventional chemotherapeutic agents can be described, in some embodiments, by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the presently disclosed subject matter refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

II. Radiotracer Compounds for Targeting NCEH1

PET is a non-invasive medical imaging technique that relies on the detection of radiation emitted by a radionuclide introduced in the body of the subject on a biologically active molecule. Images of the radionuclide's localization can be reconstructed by computer analysis providing quantitative maps of the radionuclide's distribution in the body of the subject. Such images can provide valuable information of the biochemistry and physiology of a subject. Because PET is a molecular imaging technique, it can detect cellular abnormalities before anatomical changes have occurred.

The most common radioisotopes used in PET are $^{18}$F, $^{15}$O, $^{13}$N and $^{11}$C, with half-lives of 110, 2, 10, and 20 min respectively. $^{18}$F is usually preferred due to its longer half-life and its lower positron energy which results in better resolution. Despite the relatively short half-life of these radioisotopes, they are widely used in medical diagnostics as many hospitals have their own cyclotron to prepare the radionuclides or have a nearby facility that can prepare the radionuclides.

In some embodiments, preparation of PET agents can comprise substituting $^{18}$F (or another radioactive halogen isotope) for a hydroxy (—OH) or hydrogen (—H) moiety of a base molecule (also referred to herein as a "precursor compound"). Such substitution generally preserves the biological properties of the base molecule and renders the molecule suitable for imaging using PET or single-photon emission computed tomography (SPECT) cameras. For example, substitution of the hydroxy in position 2 of glucose with $^{18}$F does not alter the capability to be uptaken by cells.

According to one aspect, the presently disclosed subject matter provides a radiotracer compound that combines the selective targeting capacity of a covalent activity-based probe with the imaging power of PET to create an activity-based radiotracer targeting the lipid hydrolase, neutral cholesterol ester hydrolase 1 (NCEH1, also known as AADACL1 or KIAA1363). The presently disclosed radiotracer compounds for example, comprise a carbamate compound with a leaving group that can impart NCEH1 specificity attached to the carbamate moiety oxygen atom and a radiolabeled group attached to the nitrogen atom of the carbamate moiety. The radiolabeled moiety becomes covalently attached to the NCEH1 upon reaction of the radiotracer compound and an active site nucleophile in the enzyme. These compounds inhibit NCEH1 with high potency and specificity in cells and in vivo is demonstrated herein below. For example, these compounds can provide direct visualization of active NCEH1 in the microenvironment of aggressive triple-negative breast cancer xenograft tumors, as well as other tumors, such as prostate tumors.

In some embodiments, the presently disclosed subject matter provides a compound (i.e., a radiotracer compound) having the formula:

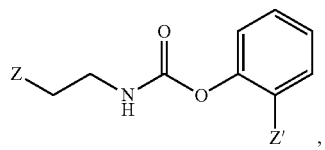

where Z' is selected from alkyl (e.g., straight chain alkyl (n-alkyl) or branched alkyl), cycloalkyl (e.g., cyclopentyl), heterocyclic, aryl, heteroaryl, and heterocyclic; and Z is selected from —Ar$_1$—O-L-R and —NH—C(=O)—Ar$_2$—O-L-R, wherein Ar$_1$ and Ar$_2$ are each aryl, heteroaryl, heterocyclic, substituted aryl, substituted heteroaryl, or substituted heterocyclic; L is alkylene (e.g., C1-C6 alkylene); and R is a halogen radioisotope (e.g., $^{18}$F, $^{35}$Cl, $^{75}$Br, $^{76}$Br, $^{77}$Br, $^{82}$Br, $^{123}$I, $^{124}$I, $^{125}$I, $^{131}$I, or $^{211}$At). In some embodiments, e.g., for use in SPECT, the compound can include a gamma-emitting radioactive halogen isotope, e.g., $^{123}$I, $^{131}$I, or $^{77}$Br. In some embodiments, e.g., for use in PET, the compound can comprise a positron-emitting radioactive halogen isotope, e.g., $^{18}$F or $^{124}$I.

In some embodiments, Z' is C1-C6 n-alkyl or branched alkyl, such as, but not limited to, methyl, ethyl, n-propyl, iso-propyl, n-butyl, iso-butyl, sec-butyl, tert-butyl, n-pentyl, sec-pentyl, 3-pentyl, sec-isopentyl, 2-methylbutyl, n-hexyl, and 3-methylpentyl. In some embodiments, Z' is selected from cycloalkyl (e.g., cyclopentyl, cyclopropyl, cyclohexyl), heterocyclic and heteroaryl; (e.g., furanyl, morpholinyl, pyranyl, pyridinyl, thiophenyl, and pyrimidinyl). In some embodiments, Z' is isopropyl and the compound has a structure of the formula:

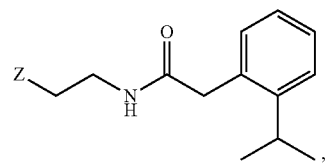

wherein Z is selected from —Ar$_1$—O-L-R and —NH—C(=O)—Ar$_2$—O-L-R, wherein Ar$_1$ and Ar$_2$ are each aryl, heteroaryl, heterocyclic, substituted aryl, substituted heteroaryl, or substituted heterocyclic; L is alkylene (e.g., C1-C6 alkylene); and R is a halogen radioisotope.

In some embodiments, Ar$_1$ and Ar$_2$ are selected from aryl and substituted aryl. In some embodiments, Ar$_1$ and Ar$_2$ are selected from phenyl and naphthyl. In some embodiments, Ar$_1$ is phenyl. In some embodiments, Ar$_2$ is naphthyl. In some embodiments, L is ethylene (i.e., —CH$_2$CH$_2$—) or propylene (i.e., —CH$_2$—CH$_2$—CH$_2$—).

In some embodiments, the compound has a structure of the formula:

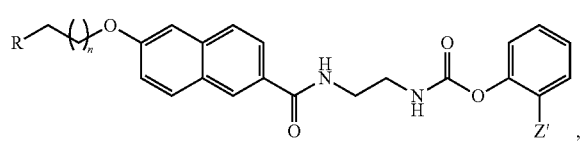

wherein Z' and R are as defined above and n is an integer between 0 and 5 (i.e., 0, 1, 2, 3, 4, or 5). In some embodiments, Z' is isopropyl and the compound has the structure:

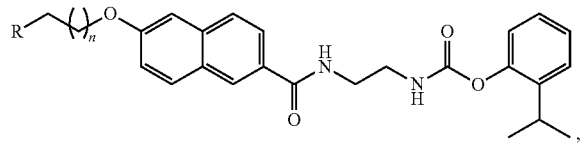

wherein n is an integer between 0 and 5 (e.g., 2 or 3); and R is a halogen radioisotope (e.g., $^{18}$F). In some embodiments, the compound has the structure:

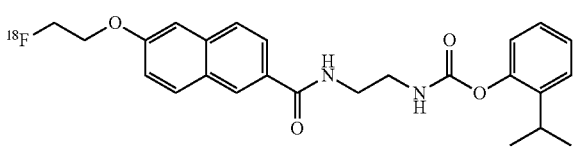 [SMILES: CC(C)c1ccccc1OC(=O)NCCNC(=O)c1ccc2cc(OCC[18F])ccc2c1]

(i.e., [$^{18}$F]JW291).

In some embodiments, the compound has a structure of the formula:

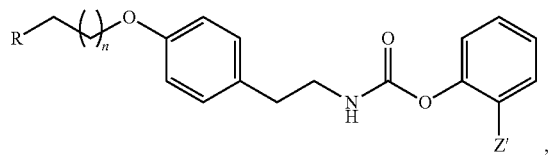

wherein R and Z' are as defined above and n is an integer between 0 and 5. In some embodiments, Z' is isopropyl and the compound has a structure of the formula:

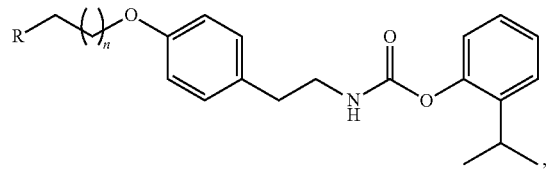

wherein n is an integer between 0 and 5 (i.e., 0, 1, 2, 3, 4 or 5) and R is a halogen radioisotope. In some embodiments, n is 1 or 2. In some embodiments, R is selected from the group comprising $^{18}$F, $^{36}$Cl, $^{75}$Br, $^{76}$Br, $^{77}$Br, $^{82}$Br, $^{123}$I, $^{124}$I, $^{125}$I, $^{131}$I, and $^{211}$At. In some embodiments, R is $^{18}$F. In some embodiments, n is 1.

In some embodiments, the compound is selected from:

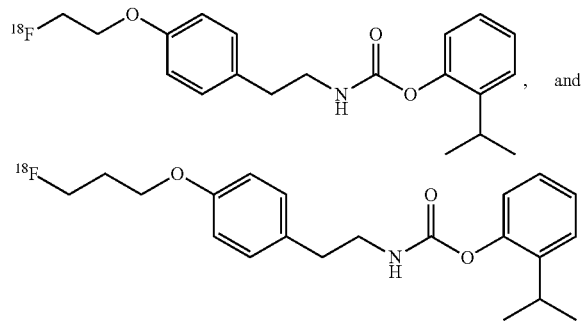

(i.e., [$^{18}$F]JW199 or [$^{18}$F]JW245).

In some embodiments, the compound is provided in a radiopharmaceutical composition wherein the compound is admixed with a pharmaceutically acceptable carrier. Any suitable pharmaceutical formulation can be used to prepare the compositions for administration to a subject. In some embodiments, the composition and/or carriers can be pharmaceutically acceptable in humans.

The "pharmaceutically acceptable carrier" is typically a fluid, e.g., a liquid, in which the in vivo imaging agent or tracer compound is suspended or dissolved, such that the composition is physiologically tolerable, i.e., can be administered to the mammalian or other subject body without toxicity or undue discomfort. In some embodiments, the pharmaceutically acceptable carrier is an injectable carrier liquid such as sterile, pyrogen-free water for injection; an aqueous solution such as saline (which can be balanced so that the final product for injection is either isotonic or not hypotonic); an aqueous solution of one or more tonicity-adjusting substances (e.g. salts of plasma cations with pharmaceutically acceptable counterions), sugars (e.g. glucose or sucrose), sugar alcohols (e.g. sorbitol or mannitol), glycols (e.g. glycerol), or other non-ionic polyol materials (e.g. polyethyleneglycols (PEGs), propylene glycols (PPGs) and the like). The pharmaceutically acceptable carrier can also comprise pharmaceutically acceptable organic solvents such as ethanol. Such organic solvents are useful to solubilize more lipophilic compounds or formulations. In some embodiments, the pharmaceutically acceptable carrier is pyrogen-free water for injection, isotonic saline or an aqueous ethanol solution. The pH of the pharmaceutically acceptable carrier for intravenous injection can be in the range 4.0 to 10.5.

In some embodiments, the radiopharmaceutical composition comprises an aqueous solution. Such a composition can optionally contain further ingredients such as buffers; pharmaceutically acceptable solubilizers (e.g. cyclodextrins or surfactants such as poloxamers, polysorbates, or phospholipids); pharmaceutically acceptable stabilizers or anti-oxidants (such as ascorbic acid, gentisic acid or para-aminobenzoic acid).

In some embodiments, the radiopharmaceutical composition is an aqueous or non-aqueous sterile injection solution that can contain anti-oxidants, buffers, bacteriostatics, bactericidal antibiotics, and solutes that render the formulation isotonic with the bodily fluids of the subject; or an aqueous or non-aqueous sterile suspension that can include suspending agents and thickening agents. Some exemplary ingredients are sodium dodecyl sulfate (SDS), in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above, the formulations of this presently disclosed subject matter can include other agents conventional in the art having regard to the type of formulation in question. For example, sterile pyrogen-free aqueous and non-aqueous solutions can be used.

III. Methods for Labeling NCEH1 and for Visualizing Tumors

In some embodiments, the presently disclosed subject matter provides a method of labeling (i.e., covalently labeling) NCEH1. In some embodiments, the method comprises contacting a sample with a tracer compound as described above, i.e., a compound having a structure:

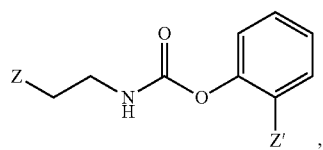

where Z' is selected from alkyl (e.g., n-alkyl or branched alkyl), cycloalkyl (e.g., cyclopentyl), heterocyclic, aryl, heteroaryl, and heterocyclic; and Z is selected from —Ar$_1$—O-L-R and —NH—C(=O)—Ar$_2$—O-L-R, wherein Ar$_1$ and Ar$_2$ are each aryl, heteroaryl, heterocyclic, substituted aryl, substituted heteroaryl, or substituted heterocyclic; L is alkylene (e.g., C1-C6 alkylene), and R is a halogen radioisotope (e.g., $^{18}$F, $^{36}$Cl, $^{75}$Br, $^{76}$Br, $^{77}$Br, $^{82}$Br, $^{123}$I, $^{124}$I, $^{125}$I, $^{131}$I, or $^{211}$At).

In some embodiments, Z' is C1-C6 n-alkyl or branched alkyl. In some embodiments, Z' is isopropyl and the compound has a structure of the formula:

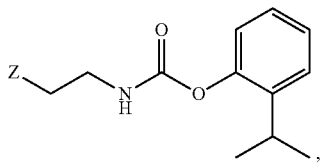

where Z is selected from —Ar$_1$—O-L-R and —NH—C(=O)—Ar$_2$—O-L-R, wherein Ar$_1$ and Ar$_2$ are each aryl, heteroaryl, heterocyclic, substituted aryl, substituted heteroaryl, or substituted heterocyclic L is alkylene (e.g., C1-C6 alkylene), and R is a halogen radioisotope.

In some embodiments, Ar$_1$ and Ar$_2$ are selected from aryl and substituted aryl. In some embodiments, Ar$_1$ and Ar$_2$ are selected from phenyl and naphthyl. In some embodiments, Ar$_1$ is phenyl. In some embodiments, Ar$_2$ is naphthyl. In some embodiments, L is ethylene (i.e., —CH$_2$CH$_2$—) or propylene (i.e., —CH$_2$—CH$_2$—CH$_2$—). In some embodiments, the compound has a structure of the formula:

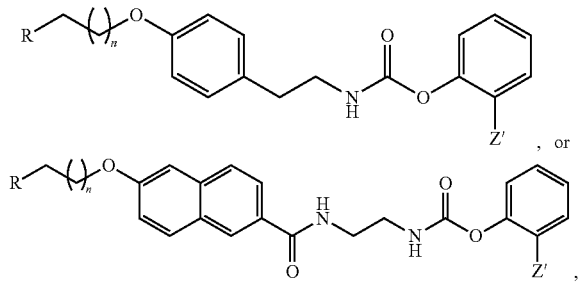

wherein R and Z' are as defined above and n is an integer between 0 and 5.

In some embodiments, the compound has a structure of the formula:

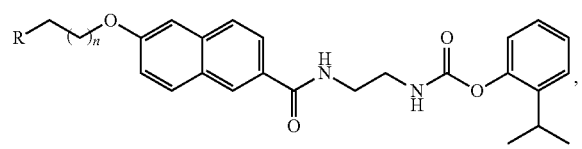

wherein n is an integer between 0 and 5 (e.g., 2 or 3); and R is a halogen radioisotope (e.g., $^{18}$F). In some embodiments, the compound is [$^{18}$F]JW291.

In some embodiments, the compound has a structure of the formula:

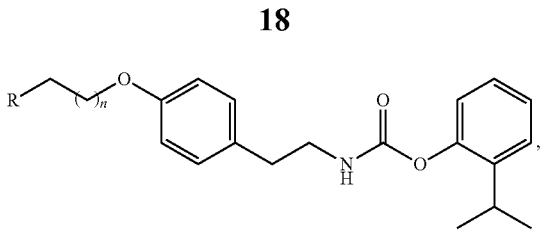

wherein n is an integer between 0 and 5 (i.e., 0, 1, 2, 3, 4 or 5) and R is a halogen radioisotope. In some embodiments, n is 1 or 2. In some embodiments, R is selected from the group comprising $^{18}$F, $^{36}$Cl, $^{75}$Br, $^{76}$Br, $^{77}$Br, $^{82}$Br, $^{123}$I, $^{124}$I, $^{125}$I, $^{131}$I, and $^{211}$At. In some embodiments, R is $^{18}$F. In some embodiments, n is 1. In some embodiments, the compound is [$^{11}$F]JW199 or [$^{18}$F]JW245.

The sample can comprise any sample known or suspected of containing NCEH1. In some embodiments, the sample comprises a biological sample such as one of the group comprising a cell, a cell culture, a tissue, an organ, and a subject. In some embodiments, the method can further include allowing the compound to contact the sample for a period of time (e.g., a few minutes or hours), treating the sample to remove any unreacted radiotracer compound (e.g., via a washing, extraction step, and/or other purification step) and detecting a signal (e.g., gamma emission or positron emission) emitted by any radioisotope remaining in the sample due to reaction and covalent bonding between the NCEH1 and the radiotracer compound, resulting in the labeling of the NCEH1 with the radiolabeled moiety from the radiotracer compound. In some embodiments, the method can further comprise determining the amount of NCEH1 in the sample by comparing the detected signal with a signal from a sample comprising a known amount of NCEH1.

In some embodiments, the presently disclosed subject matter provides a method of imaging or visualizing a tumor (e.g., a cancerous tumor). In some embodiments, the tumor is imaged or visualized in vivo, i.e., in an intact subject. In some embodiments, the method comprises (a) administering a tracer compound to a subject having or suspected of having a tumor, wherein the tracer compound is a compound of the presently disclosed subject matter, i.e., having the formula:

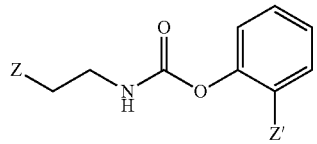

where Z' is selected from alkyl (e.g., n-alkyl or branched alkyl), cycloalkyl (e.g., cyclopentyl), heterocyclic, aryl, heteroaryl, and heterocyclic; and Z is selected from —Ar$_1$—O-L-R and —NH—C(=O)—Ar$_2$—O-L-R, wherein Ar$_1$ and Ar$_2$ are each aryl, heteroaryl, heterocyclic, substituted aryl, substituted heteroaryl, or substituted heterocyclic; L is alkylene (e.g., C1-C6 alkylene), and R is a halogen radioisotope (e.g., $^{18}$F, $^{36}$Cl, $^{75}$Br, $^{76}$Br, $^{77}$Br, $^{82}$Br, $^{123}$I, $^{124}$I, $^{125}$I, $^{131}$I, or $^{211}$At); and (b) detecting radioactivity of the radioisotope from the tracer compound, thereby visualizing a tumor (or the edges thereof) when a tumor is present in said subject. In some embodiments, Ar$_1$ and Ar$_2$ are aryl or substituted aryl. In some embodiments, Z' is isopropyl.

In some embodiments, the tracer compound has a structure of the formula:

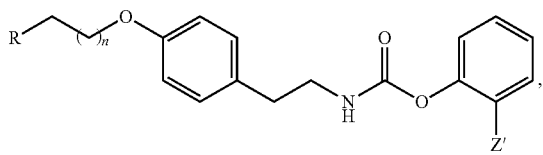

wherein Z' is selected from alkyl (e.g., n-alkyl or branched alkyl), cycloalkyl (e.g., cyclopentyl), heterocyclic, aryl, heteroaryl, and heterocyclic; n is an integer between 0 and 5 (e.g., 1 or 2); and R is a halogen radioisotope. In some embodiments, Z is C1-C6 n-alkyl or branched alkyl. In some embodiments, Z' is isopropyl. In some embodiments, R is $^{18}$F. In some embodiments, n is 1. In some embodiments, the tracer compound is selected from:

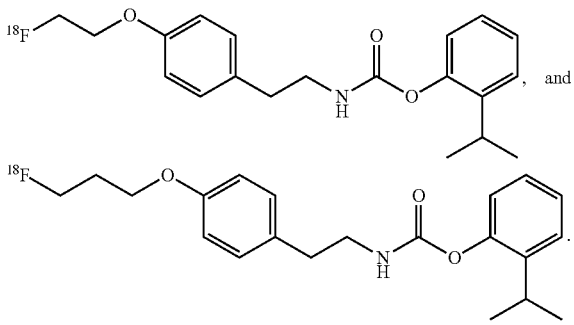

In some embodiments, the tracer compound has a structure of the formula:

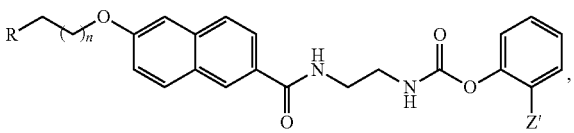

where R and Z' are as defined above and n is an integer between 0 and 5. In some embodiments, Z' is isopropyl and the compound has a structure of the formula:

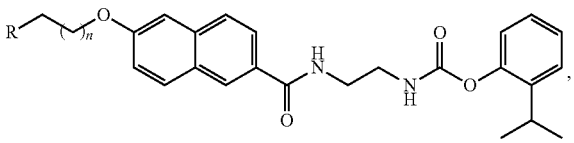

wherein n is an integer between 0 and 5 (e.g., 1 or 2) and R is a halogen radioisotope. In some embodiments, the tracer compound is [$^{18}$F]JW291.

In some embodiments, the administering is carried out parenterally. In some embodiments, the administering is administered intravenously. In some embodiments, the intravenous route represents the most efficient way to deliver the radiotracer compound throughout the body of the subject into contact with NCEH1 expressed in said subject.

For example, when the subject is an intact mammal, the radiotracer compound can dynamically move through the mammal's body, coming into contact with various tissues therein. Once the radiotracer compound comes into contact with NCEH1, covalent labeling takes place such that the radioisotope remains associated in the tissue with NCEH1. In contrast, the radiotracer is cleared faster from tissues without NCEH1. A certain point in time can be reached when detection of labeled NCEH1 is provided as a result of the ratio between radiotracer compound moiety bound to tissue with NCEH1 versus that bound in tissue without, or with less, NCEH1. When a tissue is observed to express higher levels of NCEH1 this can be an indication that this tissue is cancer tissue.

The detecting step can involve detection of signals emitted by the radioisotope of said radiotracer compound by means of a detector sensitive to said signals. This detecting step can also be understood as the acquisition of signal data. In some embodiments, the detecting is performed via SPECT and/or PET. In some embodiments, the detected signal can be analyzed, e.g., in a step carried out by a computer which applies a reconstruction algorithm to acquired signal data to yield a dataset. This dataset is then manipulated to generate images showing the location and/or amount of signal emitted by radioisotope.

In some embodiments, the detected signal (e.g., the detected and analyzed signal) can be used in the identification and/or monitoring of a tumor. For example, the method can be used to identify the presence of a tumor in said subject, preferably as an aid to making a diagnosis, in selecting an appropriate treatment or in the determination of a patient's prognosis. In the context of identifying the presence of a tumor, the information obtained upon analysis of the detected signal can be compared with data obtained using the same method carried out on a cohort of normal subjects, i.e. subjects known not to be suffering from cancer. In this way any significant deviation from the normal value for NCEH1 expression can be determined, and this deviation can be attributed to a particular clinical picture. For monitoring said tumor, the information can be compared with data obtained at an earlier point in time using the same method carried out on the same subject. Differences between the information obtained at the various time points can indicate progression or regression of the tumor. The method can also encompass monitoring to evaluate the success of a treatment, or in the determination of the potential efficacy of a test compound as a new treatment. Thus, it is envisaged that the method of the presently disclosed subject matter can also be applied in a pre-clinical setting in the testing and optimization of treatments under development.

Accordingly, in some embodiments, the subject is known to have a tumor and the method can involve determining the efficacy of a treatment administered to eliminate or reduce the tumor. The treatment can be a treatment known to treat tumors, such as a known chemotherapeutic agent or radiotherapy. Alternatively, the treatment can be a potential chemotherapeutic agent that is being tested for efficacy in vivo or for use in treating a particular type of tumor. Thus, in some embodiments, the method further comprises: (c) administering a cancer treatment or a potential cancer treatment to the subject; (d) repeating steps (a) and (b), thereby re-visualizing the tumor visualized in step (b); and (e) comparing the tumor as visualized in step (b) to the tumor as visualized in step (d), thereby determining the in vivo effectiveness of the cancer treatment or the potential cancer treatment. In some embodiments, the cancer treatment or potential cancer treatment is a pharmaceutical agent (e.g., a natural or synthetic small molecule) known or suspected to treat cancer. In some embodiments, comparing the tumor as visualized in step (b) to the tumor as visualized in step (d)

comprises comparing the size of the tumor visualized in step (b) to the size of the tumor visualized in step (d).

In some embodiments, the method comprises (a) administering a tracer compound to a subject known or suspected of having a tumor; (b) detecting radioactivity of the radioisotope from the tracer compound, thereby visualizing a tumor (or the edges thereof) present in said subject; and further comprising administering a cancer treatment to said subject to treat said tumor. The cancer treatment can be any treatment suitable for treating the tumor. In some embodiments, the cancer treatment is surgery, radiation, chemotherapy, toxin therapy, immunotherapy, cryotherapy, gene therapy, or any combination thereof. In some embodiments, the cancer treatment is surgery, radiation, or chemotherapy. In some embodiments, the cancer treatment is administered directly to the visualized tumor.

In some embodiments, the subject is a mammal. In some embodiments, the subject is a human. In some embodiments, the subject is a subject who has been diagnosed with cancer, who has been previously treated for cancer, or who has an elevated risk factor for cancer (e.g., based on age, a family history of a cancer, or exposure to a cancer-causing chemical).

In some embodiments, the tumor visualized by the methods disclosed herein is a tumor related to breast cancer or prostate cancer. In some embodiments, the breast cancer is a triple negative breast cancer.

IV. Subjects

The methods and compositions disclosed herein can be used on a sample either in vitro (for example, on isolated cells or tissues) or in vivo in a subject (i.e. living organism, such as a patient). In some embodiments, the subject or patient is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

V. Doses

In some embodiments, an effective dose of a radiopharmaceutical composition of the presently disclosed subject matter is administered to a subject. An "effective amount" of the tracer compound is an amount of the radiopharmaceutical composition sufficient to produce detectable signal. Actual dosage levels of constituents of the compositions of the presently disclosed subject matter can be varied so as to administer an amount of the composition that is effective to achieve the desired effect for a particular subject and/or target. The selected dosage level can depend upon the activity of the composition and the route of administration.

After review of the disclosure herein of the presently disclosed subject matter, one of ordinary skill in the art can tailor the dosages to an individual subject, taking into account the particular formulation, method of administration to be used with the composition, and nature of the target to be visualized. Such adjustments or variations, as well as evaluation of when and how to make such adjustments or variations, are well known to those of ordinary skill in the art.

VI. Synthesis

As used herein, the term "precursor compound" comprises a non-radioactive derivative of a radiolabeled compound of the presently disclosed subject matter, designed so that chemical reaction with a convenient chemical form of the radioisotope occurs site-specifically; can be conducted in the minimum number of steps (ideally a single step); and without the need for significant purification (ideally no further purification), to give the desired radiotracer compound. Such precursor compounds are synthetic and can conveniently be obtained in good chemical purity.

The term "a convenient chemical form of a radioisotope" means the radioisotope in a chemical form that is reactive with a substituent of the precursor compound such that the radioisotope becomes covalently attached to the precursor compound. For each particular radioisotope suitable for inclusion in a radiotracer compound of the presently disclosed subject matter, there are one or more suitable sources of the radioisotope. The person skilled in the art of in vivo imaging agents will be familiar with these and other sources of radioisotopes that are suitable for application in the presently disclosed subject matter.

When the radioisotope of the tracer compound is $^{18}$F, labelling with $^{18}$F can be achieved by nucleophilic displacement of a leaving group from a precursor compound. Suitable leaving groups include —Cl, —Br, —I, tosylate (OTs), mesylate (OMs) and triflate (OTf). Another strategy would be to have a suitable leaving group in place on an alkylamide group present on the precursor compound. In both cases, the precursor compound can be labeled in one step by reaction with a suitable source of [$^{18}$F]-fluoride ion ($^{18}$F$^-$), which is normally obtained as an aqueous solution from the nuclear reaction $^{18}$O(p,n)$^{18}$F and is made reactive by the addition of a cationic counterion and the subsequent removal of water. $^{18}$F can also be introduced by O-alkylation of hydroxy groups in the precursor compound with $^{18}$F(CH$_2$)$_3$-LG wherein LG represents a leaving group as defined above. Alternatively, the radiofluorine atom can attach via a direct covalent bond to an aromatic ring such as a benzene ring. For aryl systems, $^{18}$F-fluoride nucleophilic displacement from an aryl diazonium salt, aryl nitro compound or an aryl quaternary ammonium salt are suitable routes to aryl-$^{18}$F derivatives.

Thus, in some embodiments, [$^{18}$F]-labelling of a precursor compound can be performed by nucleophilic substitutions with a source of [$^{18}$F]fluoride. Electrophilic substitutions can however also be used. Nucleophilic substitutions (aliphatic and aromatic) with [$^{18}$F]fluoride can be performed either on an immediate precursor of the target molecule (direct labelling using a one-step process) or on an indirect precursor followed by one or more chemical steps leading to the target radiotracer.

There is no particular restriction on the nature of the sources of [$^{18}$F]fluorides to be used, and any sources of [$^{18}$F]fluorides conventionally used in the art can be used, provided that it has no adverse effect on other parts of the molecule. Examples of suitable sources of [$^{18}$F]fluorides include: alkali metal [$^{18}$F]fluorides, such as sodium [$^{18}$F]fluoride, potassium [$^{18}$F]fluoride, cesium [$^{18}$F]fluoride; ammonium [$^{18}$F]fluoride, and tetraalkylammonium [$^{18}$F]fluorides, such as tetrabutylammonium [$^{18}$F]fluoride. In some embodiments, the source of [$^{18}$F] fluoride is an alkali metal [$^{18}$F]fluoride, e.g. a potassium [$^{18}$F]fluoride. The source of [$^{18}$F]fluoride can be activated by the presence of a ligand able to complex the counter cationic species of the source of [$^{18}$F]fluoride. The ligand can be a cyclic or polycyclic multidentate ligand. Examples of suitable ligands include, for example, crown ethers such as 1,4,7,10,13-pentaoxacyclooctadecane or cryptands sold under the tradename KRYPTOFIX™ (Merck, Darmstadt, Germany) such as 4,7,13,16,21,24-hexaoxa-1,10-diazabicyclo-[8,8,8]hexacosane sold under the name KRYPTOFIX™ 222 (Merck, Darmstadt, Germany). In some embodiments, the source of [$^{18}$F]fluoride is an alkaline metal [$^{18}$F]fluoride/cryptate complex. In some embodiments, the source is a potassium [$^{18}$F]fluoride/cryptate complex, such as, but not limited to a potassium [$^{18}$F]fluoride/4,7,13,16,21,24-hexaoxa-1,10-diazabicyclo-[8,8,8]hexacosane complex In some embodiments, when the tracer compound comprises a radioisotope of iodine or bromine, the precursor compound can comprise a derivative which undergoes electrophilic iodination or electrophilic bromination. Examples of suitable derivatives include organometallic derivatives such as a trialkylstannane (e.g. trimethylstannyl or tributylstannyl), or a trialkylsilane (e.g. trimethylsilyl) or an organoboron compound (e.g. boronate esters or organotrifluoroborates). In some embodiments, radioiodination of a precursor compounds can be performed by an exchange, e.g., in acidic conditions, between a non-radioactive iodinated precursor molecule and an alkaline radioactive halide. The exchange can be carried out, for example under a temperature in a range of 100 to 200° C., using an aqueous solution of a precursuor compound and a radioactive halide, e.g., [$^{125}$I]NaI, in buffered medium or in acetic acid, optionally in the presence of a catalyst such as, for example, copper(II) sulfate. Radiolabelling can also be performed between a trialkylstannane precursor compound and an alkaline halide, such as [$^{125}$I]NaI or [$^{131}$I]NaI, in the presence of an oxidative agent as chloramine-T, peracetic acid, or hydrogen peroxide or in the presence of an acid as hydrochloric acid, acetic acid or an acid buffer solution, preferentially at room temperature and in an appropriate solvent.

Precursor compounds for preparing tracer compounds (e.g., in vivo imaging agents) can be provided in sterile, apyrogenic form in order to be used for the preparation of a radiopharmaceutical composition comprising the in vivo imaging agent together with a pharmacologically-acceptable carrier suitable for mammalian administration to a subject (e.g., a human or other mammal). The precursor compound is also suitable for inclusion as a component in a kit or a cassette for the preparation of such a radiopharmaceutical composition. The precursor compound can be bound to a solid phase and can be supplied covalently attached to a solid support matrix. In this way, the desired product forms in solution, whereas starting materials and impurities remain bound to the solid phase. As an example of such a system, precursor compounds for solid phase electrophilic fluorination with $^{18}$F-fluoride are described in International Publication No. WO 2003/002489 (the disclosure of which is incorporated herein by reference in its entirety), and precursor compounds for solid phase nucleophilic fluorination with $^{18}$F-fluoride are described in International Publication No. WO 2003/002157 (the disclosure of which is incorporated herein by reference in its entirety). Alternatively, the precursor compound can be provided in solution in a kit or in a cassette suitable for use with an automated synthesis apparatus.

In a kit, the precursor compound can be presented in a sealed container which permits maintenance of sterile integrity and/or radioactive safety, plus optionally an inert headspace gas (e.g. nitrogen or argon), whilst permitting addition and withdrawal of solutions by syringe. An example of a sealed container is a septum-sealed vial, wherein the gastight closure is crimped on with an overseal (typically of aluminum). Such sealed containers have the advantage that the closure can withstand vacuum if desired e.g. to change the headspace gas or degas solutions. The precursor compound for use in the kit can be employed under aseptic manufacture conditions to give the desired sterile, non-pyrogenic material. The precursor compound can alternatively be employed under non-sterile conditions, followed by terminal sterilization using e.g. gamma-irradiation, autoclaving, dry heat or chemical treatment (e.g. with ethylene oxide). Typically, all components of the kit are disposable to minimize the possibilities of contamination between runs and to ensure sterility and quality assurance. Certain in vivo imaging agents, and in particular those labelled with $^{18}$F are now often conveniently prepared on an automated radiosynthesis apparatus. There are several commercially available examples of such apparatus, including, but not limited to those sold under the tradenames TRACERLAB™ and FASTLAB™ (General Electric Company, Schenectady, New York, United States of America). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. A typical such cassette comprises: (i) a vessel containing a precursor compound; and (ii) inlets and outlets for eluting the vessel with a suitable source of said radioisotope suitable for in vivo imaging as described herein. The cassette can optionally additionally comprise: (iii) an ion-exchange cartridge for removal of excess radioisotope; and/or (iv) where the precursor compound comprises one or more protecting groups, a cartridge for deprotection of the resultant radiolabelled product to form the desired in vivo imaging agent. When the in vivo imaging agent is administered as a radiopharmaceutical composition as described above, the method for preparation of said in vivo imaging agent can further comprise a step or steps to obtain a radiopharmaceutical composition, e.g. removal of organic solvent, addition of a pharmacologically-acceptable carrier and any optional further ingredients. For parenteral administration, steps to ensure that the radiopharmaceutical composition is sterile and apyrogenic can be undertaken.

Figure 4:
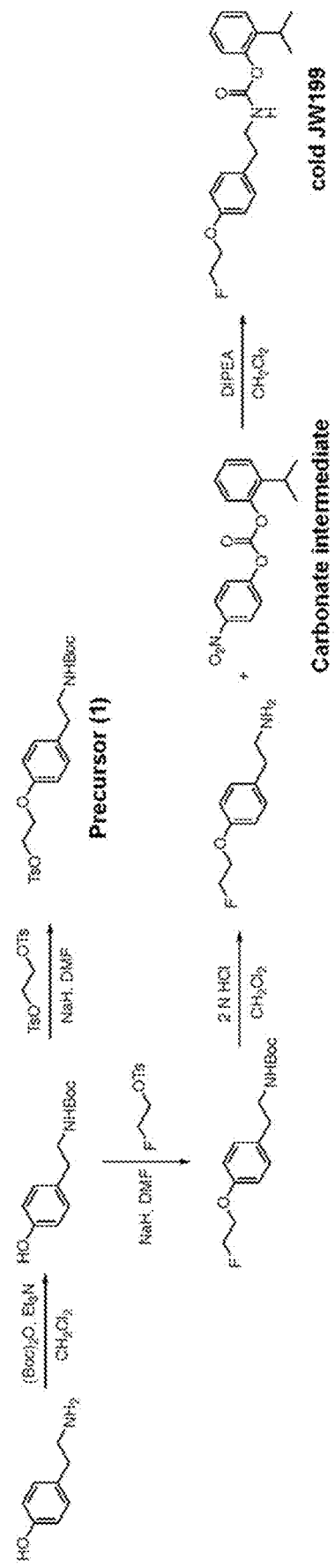
FIG. 4 is a schematic diagram showing synthetic route for 2-(4-(2-((tert-butoxycarbonyl)amino)ethyl)phenoxy)ethyl-4-methylbenzenesulfonate (precursor 1) and non-radiolabeled 2-isopropylphenyl-(4-(2-fluoroethoxy)phenethyl)carbamate (cold JW199).

In some embodiments, the presently disclosed tracer compounds can be prepared by reacting a suitable halogen radioisotope-labelled (e.g., a fluorine-18-labeled) amine with a suitable carbonate intermediate, such as 2-isopropylphenyl (4-nitrophenyl)carbonate. See FIG. 4, "Carbonate intermediate". The radioisotope-labelled amine, for example, can be prepared by reacting a protected amine comprising a suitable leaving group (e.g., tosyl (Ts) or mesyl (Ms)) with a source of halogen radioisotope (e.g., [$^{18}$F]NaF or [$^{18}$F]KF) in the presence of a cryptand and then removing the amine protecting group. In some embodiments, the protected amine is 2-(4-(2-((tert-butoxycarbonyl)amino) ethyl)phenoxy)ethyl-4-methylbenzenesulfonate or 3-(4-(2-((tert-butoxycarbonyl)amino)ethyl)phenoxy)propyl-4-methylbenzenesulfonate. In some embodiments, the protected amine can be a N-protected (e.g., Boc-protected) 2-((6-((2-aminoethyl)carbamoyl)naphthalen-2-yl)oxy)ethyl-4-methylbenzenesulfonate. The protected amines can be prepared by reacting an N-protected 4-(2-aminoethyl)phenol or an N-protected N-(2-aminoethyl)-6-hydroxy-2-naphthamide with a bis-(tosyloxy)alkane (e.g., 1,2-bis(tosyloxy)ethane or 1,3-bis(tosyloxy)propane).

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Synthesis of Radiolabeled JW199

Carrier-free [$^{18}$F]-fluoride anions were produced by the 18O(p, n)$^{18}$F nuclear reaction with a 18 MeV proton beam generated by the IBA Cyclone® 18/9 cyclotron (Ion Beam Applications; IBA; Louvain-la-neuve, Belgium) in a niobium target using isotopically enriched [$^{18}$O]—H$_2$O (Medical Isotopes Inc. Pelham, New Hampshire, United States of America). The target entrance window is made of Havar. An aluminum disk is used as an energy degrader to slightly lower the beam energy to better match the production cross section for $^{18}$F but is not in contact with the target liquid. Typical irradiation parameters were 20-60 microampere (μA) of protons for 30-120 minutes. Yields of $^{18}$F are roughly linear with beam current, up to >5 curie (Ci) for a 2-hour irradiation. The [$^{18}$F]-fluoride, as HF, is transferred from the target to the designated synthesis box using helium (He) gas (ultra high purity (UHP) grade, 99.999%).

A Synthera® V2 synthesis module with HPLC capabilities (IBA, Louvain-la-neuve, Belgium) was used for the synthesis. The Nucleophilic Integrated Fluidic Processor (IFP) kit was purchased from Advanced Biochemical Compounds (Radeberg, Germany) and used without any modifications. A custom-built work-up frame was used to reconstitute the radiolabeled compound into injectable dose form using solid phase extraction cartridges. For quality control, an Agilent Infinity 1260 HPLC system (Agilent Technologies Inc., Santa Clara, California, United States of America) equipped with a vial sampler (G7129A, Agilent Infinity II series), 1260 VWD detector (G7114A, Agilent Infinity II series) and a 1260 Isocratic Pump (G7110B, Agilent Infinity II series), was used. The system was operated by Laura radiochromatography-HPLC software (LabLogic Systems, Ltd., Sheffield, United Kingdom). The stationary phase analytical column was a Phenomenex Luna C-18(2) 100 Å (00G-4252-E0), 5 μm RP column, 250×4.6 mm (Phenomenex, Torrance, California, United States of America). A mixture of 70% acetonitrile in water acidified with 0.1% trifluoroacetic acid (TFA) was used as the mobile phase and an isocratic elution technique was used for analysis within 0-15 minutes. For the detection of radioactive compounds, an Eckert & Ziegler Flow-Count radio-HPLC detection system (Eckert & Ziegler Radiopharma, Inc., Hopkinton, Massachusetts, United States of America) with a PEARL interface (LabLogic Systems Ltd., Sheffield, United Kingdom) was used. Specific radioactivity was measured by HPLC using a standard mass curve of known concentrations of [$^{18}$F]JW199.

The following V2 module was used for synthesis of [$^{18}$F]JW199:
Vial 1: Eluent (15 mg kryptofix 2.2.2 (40 μmol) in 0.8 mL of acetonitrile and 1.4 mg K2CO3 (10 μmol)) in 0.2 mL of water
Vial 2: Precursor 1, 3 mg (6.9 μmol) in 0.8 mL acetonitrile (MeCN)
Vial 3: Trifluoroacetic acid (TFA), 150 mg (1.31 mmol) in 0.9 mL methylene chloride
Vial 4: Carbonate intermediate3, 7 mg (23.2 μmole) plus diisopropylethylamine, 250 μL in methylene chloride, 750 μL.

A syringe outside of the hotcell was filled with 5 mL of 60% acetonitrile in water and connected to the reaction vessel using ¹⁄₁₆ inch-38-eflon tubing, four-way stopcock sold under the tradename DISCOFIX™ (B. Braun Medical Inc., Melsungen, Germany) and a needle inserted through the septum. After loading the reagents, a pre-synthesis check was performed using the written program for [$^{18}$F]JW199. [$^{18}$F]-Fluoride from the target was trapped on a QMA ion exchange cartridge (Waters Corporation, Milford, Massachusetts, United States of America) and eluted using the contents of vial 1. The [$^{18}$F]-kryptofix complex was dried at 110° C. for 5 min and 95° C. for 4 min under periodic vacuum and helium flow. After final drying, the precursor 1 was added from vial 2 and labelling was achieved by heating to 100° C. for 10 min. The solvent (MeCN) was dried under vacuum and helium flow for 4 min, followed by addition of diluted TFA from vial 3 of the IFP kit and incubation at 40° C. for 5 min. The basic carbonate solution was then added from vial 4 to the [$^{18}$F]-labeled, deprotected, precursor and the solution was heated to 40° C. for 5 min. The crude reaction mixture was then purified by the Synthera® HPLC system (IBA, Louvain-la-neuve, Belgium) equipped with a Symmetry® Prep C18 7 μm 10×300 mm column (Waters Corporation, Milford, Massachusetts, United States of America, WAT066245) and a constant eluent flow of 60% MeCN acidified by 0.1% TFA at a speed of 9.5 mL/min. The [$^{18}$F]JW199 peak was collected between 26-29 min, transferred into the remote controlled, custom-built, vacuum-driven, work-up frame where it was diluted in 60 mL of water and subsequently trapped on a preconditioned solid phase extraction cartridge sold under the trade name SEP-PAK™ C-18 Plus (Waters Corporation) solid phase extraction cartridge. After washing the extraction cartridge with 5 mL of water and drying under vacuum, [$^{18}$F]JW199 was eluted to the final product vial with 1 mL of EtOH from the work-up frame. 9 mL of 0.9% saline was then passed through the C18 cartridge from the work-up frame to the final product vial. The synthesis and dose preparation were done in an ISO Class 7 Comecer Hotcell (Comecer, Castel Bolognese, Italy). The prepared final dose was sent to an ISO Class 6 Comecer laminar flow hotcell (Comecer, Castel Bolognese, Italy) for dispensing.

Dry solvents were obtained by passing through activated alumina columns. All reactions were carried out under inert atmospheric nitrogen using oven-baked glassware, unless otherwise noted. Flash chromatography was performed using 230-400 mesh silica gel 60. NMR spectra were generated on a Bruker 500 MHz instrument (Bruker Corporation, Billerica, Massachusetts, United States of America). Chemical shifts were recorded in ppm relative to tetramethylsilane (TMS) with multiplicities given as s (singlet), bs (broad singlet), d (doublet), t (triplet), dt (double of triplets), q (quadruplet), qd (quadruplet of doublets), m (multiplet).

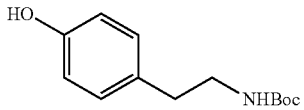

tert-butyl(4-hydroxyphenethyl)carbamate: To a solution of 4-(2-aminoethyl)phenol (3.1 g, 23.1 mmol) in dry dichloromethane (110 mL), Et$_3$N (3.5 g, 34.6 mmol) and di-tert-butyldicarbonate (7.6 g, 34.6 mmol) was added at 0° C. After stirring at 0° C. for 30 min, the reaction mixture was left to stir overnight at room temperature under N$_2$. The reaction mixture was treated with 30.0 mL of saturated aqueous NaHCO$_3$ solution. The organic layer was separated and the aqueous layer was extracted with dichloromethane. The combined organic extracts were washed with brine, dried over MgSO$_4$, filtered and concentrated. The crude product was purified by flash column chromatography using a 7:3 v/v Hexanes:EtOAc as solvent to afford the title compound (5.0 g, 92% yield) as a white solid. $^1$H NMR (500 MHz, Chloroform-d) δ 7.04-6.98 (m, 2H), 6.78 (d, J=8.5 Hz, 2H), 6.13 (s, 1H), 4.61 (s, 1H), 3.37-3.29 (m, 2H), 2.70 (t, J=7.2 Hz, 2H), 1.44 (s, 9H); 13C NMR (126 MHz, CDCl$_3$) δ 156.29, 154.77, 130.36, 129.81 (2C), 115.50 (2C), 79.64, 42.06, 35.28. 28.28 (3C); HRMS (m/z); [M+Na]+calculated for C$_{13}$H$_{19}$NO$_3$Na, 260.1263; found, 260.1237.

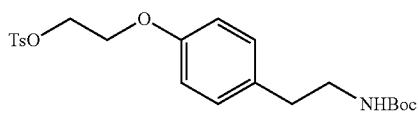 [SMILES: Cc1ccc(S(=O)(=O)OCCOc2ccc(CCNC(=O)OC(C)(C)C)cc2)cc1]

2-(4-(2-((tert-butoxycarbonyl)amino)ethyl)phenoxy) ethyl-4-methylbenzenesulfonate (Precursor, 1): To a solution of tert-butyl(4-hydroxyphenethyl)carbamate (456 mg, 1.9 mmol) in dry DMF (9 mL), NaH (116 mg, 4.8 mmol) was added at 0° C. After stirring at 0° C. for 30 min, 1,2-bis(tosyloxy)ethane (1.1 g, 2.9 mmol) was added to the reaction mixture at 0° C. and stirred overnight at room temperature under N$_2$. The reaction mixture was treated with 15.0 mL of saturated aqueous NaHCO$_3$ solution. The organic layer was separated, and the aqueous layer was extracted with EtOAc. The combined organic extracts were washed with brine, dried over MgSO$_4$, filtered and concentrated. The crude product was purified by flash column chromatography using a 7:3 v/v Hexanes:EtOAc as solvent to afford the title compound (460 mg, 55% yield) as a white solid. $^1$H NMR (500 MHz, Chloroform-d) δ 7.82 (d, J=8.2 Hz, 2H), 7.34 (d, J=7.4 Hz, 2H), 7.07 (d, J=8.2 Hz, 2H), 6.72 (d, J=8.5 Hz, 2H), 4.51 (s, 1H), 4.38-4.32 (m, 2H), 4.15-4.09 (m, 2H), 3.32 (d, J=6.7 Hz, 2H), 2.72 (t, J=7.1 Hz, 2H), 2.45 (s, 3H), 1.43 (s, 9H); 13C NMR (126 MHz, CDCl$_3$) δ 156.63, 155.86, 144.96, 132.86 (2C), 131.82, 129.87 (2C), 129.77 (2C), 128.01, 114.71 (2C), 79.19, 68.19, 65.50, 41.88, 35.25, 28.42 (3C), 21.68; HRMS (m/z): [M+Na]+ calculated for C$_{22}$H$_{29}$NO$_6$Sna, 458.1613; found, 458.1593.

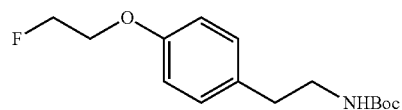 [SMILES: CC(C)(C)OC(=O)NCCc1ccc(OCCF)cc1]

tert-butyl(4-(2-fluoroethoxy)phenethyl)carbamate: To a solution of tert-butyl(4-hydroxyphenethyl)carbamate (1.0 g, 4.2 mmol) in dry DMF (20 mL), NaH (253 mg, 10.5 mmol) was added at 0° C. After stirring at 0° C. for 30 min, 2-Fluoroethyl 4-methylbenzenesulfonate (966 mg, 4.4 mmol) was added to the reaction mixture at 0° C. and stirred for 2 hr at room temperature under N$_2$. The reaction mixture was treated with 20.0 mL of saturated aqueous NaHCO$_3$ solution. The organic layer was separated, and the aqueous layer was extracted with EtOAc. The combined organic extracts were washed with brine, dried over MgSO$_4$, filtered and concentrated. The crude product was purified by flash column chromatography using a 4:1 v/v Hexanes:EtOAc as solvent to afford the title compound (1.04 g, 87% yield) as a white solid. $^1$H NMR (500 MHz, Chloroform-d) δ 7.10 (d, J=8.1 Hz, 2H), 6.86 (d, J=8.6 Hz, 2H), 4.80-4.76 (m, 1H), 4.71-4.66 (m, 1H), 4.59 (bs, 1H), 4.23-4.18 (m, 1H), 4.17-4.13 (m, 1H), 3.33 (d, J=6.8 Hz, 2H), 2.73 (t, J=7.1 Hz, 2H), 1.43 (s, 9H); 13C NMR (126 MHz, CDCl$_3$) δ 157.11, 155.97, 131.77, 129.89 (2C), 114.81 (2C), 82.06 (d, J=170.5 Hz), 79.26, 67.24 (d, J=20.4 Hz), 42.01, 35.35, 28.49 (3C); HRMS (m/z): [M+Na]+calculated for C$_{15}$H$_{22}$FNO$_3$Na, 306.1481; found, 306.1464.

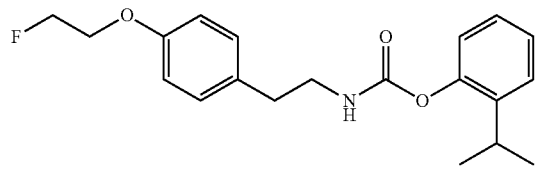 [SMILES: CC(C)c1ccccc1OC(=O)NCCc1ccc(OCCF)cc1]

2-isopropylphenyl-(4-(2-fluoroethoxy)phenethyl)carbamate (JW199): 2.0 N HCl in diethylether solution (2.9 mL, 5.8 mmol) was added to a solution of tert-butyl(4-(2-fluoroethoxy)phenethyl)carbamate (550 mg, 1.9 mmol) in dry dichloromethane (10 mL) at 0° C. After stirring at room temperature for overnight, the reaction mixture was treated with 15.0 mL of saturated aqueous NaHCO$_3$ solution.

The organic layer was separated, and the aqueous layer was extracted with dichloromethane. The combined organic extracts were washed with brine, dried over MgSO$_4$, filtered and concentrated. The crude product was used without further purification. To a solution of carbonate intermediate (584 mg, 1.9 mmol, carbonate intermediate 3 was synthesized from isopropylphenol and 4-nitrophenylchloroformate as described in U.S. Pat. No. 9,249,128, the disclosure of which is incorporated herein by reference in its entirety) in dichloromethane (10 mL) 2-(4-(2-fluoroethoxy)phenyl) ethan-1-amine (355 mg, 1.9 mmol) and DIPEA (0.8 mL, 5.8 mmol) was added at room temperature. After stirring at room temperature overnight, the reaction mixture was treated with 15.0 mL of saturated aqueous NaHCO$_3$ solution. The organic layer was separated, and the aqueous layer was extracted with dichloromethane. The combined organic extracts were washed with brine, dried over $MgSO_4$, filtered and concentrated. The crude product was purified by flash column chromatography using a 4:1 v/v Hexanes:EtOAc as solvent to afford the title compound (368 mg, 55% yield) as a white solid. $^1$H NMR (500 MHz, Chloroform-d) δ 7.28 (dd, J=5.9, 3.6 Hz, 1H), 7.20-7.12 (m, 4H), 7.05-6.99 (m, 1H), 6.89 (d, J=8.6 Hz, 2H), 5.08 (t, J=6.1 Hz, 1H), 4.82-4.76 (m, 1H), 4.72-4.67 (m, 1H), 4.25-4.19 (m, 1H), 4.19-4.14 (m, 1H), 3.49 (q, J=6.7 Hz, 2H), 3.07 (hept, J=6.9 Hz, 1H), 2.82 (t, J=7.0 Hz, 2H), 1.20 (d, J=6.9 Hz, 6H); 13C NMR (126 MHz, $CDCl_3$) δ 157.28, 154.85, 148.29, 140.68, 131.38, 129.99 (3C), 126.60, 125.99, 122.65, 114.92 (2C), 82.07 (d, J=170.5 Hz), 67.27 (d, J=20.4 Hz), 42.64, 35.20, 27.32, 23.10 (2C); HRMS (m/z): [M+H]+calculated for $C_{20}H_{24}FNO_3$, 346.1818; found, 346.1788.

Example 2

Methods and Materials

Reagents: FP-Rhodamine1 and JW576 were synthesized as described previously. See for example, U.S. Pat. No. 9,249,128, the disclosure of which is incorporated herein by reference in its entirety. All commercially available chemicals were obtained from Aldrich (Milwaukee, Wisconsin, United States of America), Acros (Fair Lawn, New Jersey, United States of America), Fisher (ThermoFisher Scientific, Waltham, Massachusetts, United States of America), Fluka (Sigma-Aldrich Holding AG, Buchs, Switzerland), or Maybridge (Altrincham, United Kingdom), and were used as received, without further purification, except where noted. Cell culture media and supplements were obtained from CellGro and Omega Scientific. The carbonate intermediate used for JW199 synthesis was produced according to previously reported procedures.[3]

Proteome Preparation: Human PC3 and MDA-MB231 cells were grown in Roswell Park Memorial Institute (RPMI) medium and Dulbecco's Modified Eagle Medium (DMEM), respectively, supplemented with 10% fetal bovine serum (FBS) and 2 mM L-glutamine, and cultured in a humidified 5% $CO_2$ incubator at 37° C. Cells were washed twice with phosphate buffered saline (PBS, pH 7.5), collected by scraping, resuspended in 0.2 ml PBS, sonicated, and fractionated via centrifugation (100,000×g, 45 min) into a pellet (containing membrane proteins) and supernatant (containing soluble proteins). For murine proteomes, mouse tissues were Dounce-homogenized on ice in cold PBS, followed by a low-speed spin (1,400×g, 5 min) to remove debris. After sonication, the membrane and soluble proteomes were fractionated as described above. All sample pellets were washed and resuspended in PBS via sonication. Protein concentrations were determined using a Bradford protein assay kit (Bio-Rad, Hercules, California, United States of America)). Samples were stored at −80° C. until use.

Cellular JW199 Treatments: JW199 was dissolved in dimethyl sulfoxide (DMSO) vehicle, which was diluted into media or buffer before addition to cells or proteomes, respectively. For in vitro proteome experiments, the final DMSO concentration was 4%. For live cell (in situ) treatments, 2×106 cells were seeded in 6 cm dishes (100% confluency) 24 hours prior to JW199 treatment in serum-free media. At the end of the experiment, cells were washed and collected, as described above, for gel-based activity profiling.

Gel-based Activity Profiling: Cell lysates were treated with 1 μM fluorophosphonate-rhodamine (FP-rho) for 30 min at room temperature (50 μL total reaction volume). Reactions were quenched with one volume of standard 4× sodium dodecyl sulfate/polyacrylamide gel electrophoresis (SDS/PAGE) reducing sample buffer, resolved on 10% acrylamide SDS/PAGE gels, and visualized in-gel with a fluorescence scanner sold under the tradename CHEMIDOC™ MP (Bio-Rad, Hercules, California, United States of America). Densitometric quantification of band intensities were used to calculate the percent inhibition via JW199. 50% inhibitory concentration ($IC_{50}$) values were determined from dose-response curves constructed in GraphPad Prism software from three independent replicates for each inhibitor concentration. For competitive ABPP with JW576, tumor lysates were treated with 1 μM JW576 for 30 min at 37° C. (50 μL total reaction volume). Competitive ABPP was then conducted as described above. NCEH1 activity was calculated by densitometric quantification (ImageJ software; National Institutes of Health (NIH), Bethesda, Maryland, United States of America) of JW576-labeled band intensity (BODIPY fluorescence) from three independent replicates.

Stability analyses of HPLC-purified [$^{O}$F]JW199: Radiochemical stability testing of the synthesized [$^{18}$F]JW199, was performed with multiple HPLC injections using increasing amounts of activity to keep the peak heights roughly similar. 64 μCi was injected 83 minutes post synthesis, and this was considered the t=0 time point. The subsequent injection was 79 μCi at 30-minutes, followed by three more injections of 86, 106, and 117 μCi at 60, 90, and 120-minutes respectively.

In vivo microPET/CT imaging: All imaging was performed by the Integrated Small Animal Imaging Research Resource (iSAIRR) at the University of Chicago (Chicago, Illinois, United States of America) on a β-Cube and X-Cube (Molecubes NV, Ghent, Belgium). Athymic nude mice (males and females, aged 6 to 8 weeks; HSD strain, Harlan-Envigo, Indianapolis, Indiana, United States of America) were anesthetized via inhalation with 1.5-2% isoflurane and injected with approximately 150 μCi (5.55 Megabecquerel (MBq)) of [$^{18}$F]JW199 in 150 μL of physiologic saline through the lateral tail vein, followed by awake incubation for 1 hour and 45 minutes. MicroCT images were acquired using the general purpose protocol, with energy of 50 KeV and a tube current of 100 μA. Respiration rate and body temperature of the animal were constantly monitored during the entire scanning period with the p-Cube and X-Cube onboard monitoring system. A 1 hr dynamic PET acquisition was started 2 hours after [$^{18}$F]JW199 injection. Dynamic reconstruction was performed for 6 frames of 10 minutes each using a three-dimensional (3D) OSEM algorithm with 400 μm isometric voxel size. For competition studies, mice were pretreated with either 80 mg/kg JW480 or vehicle (polyethylene glycol 300 (PEG300)) via oral gavage, followed 4 hours later by dosing with [$^{18}$F]JW199 and imaging as described. For the MDA-MB231 study, [$^{18}$F]JW199 injection was followed immediately by dynamic PET acquisition (90 min) and microCT scanning as detailed above. Dynamic PET image reconstruction included 9 frames of 10 minutes each.

Dynamic reconstruction was performed using a three-dimensional OSEM algorithm with 400 μm isometric voxel size. All image analysis was performed with software sold under the tradename VivoQuant™ (inviCRO, LLC, Boston, Massachusetts, United States of America). 3D regions of interest (ROIs) were drawn and standardized uptake values (SUVs) and percent injected dose per cubic centimeter of tissue (% ID/cc) were calculated for each ROI and time point. % ID/cc was calculated as a ratio of tissue radioactivity concentration (mCi/g) at time of scan to total injected activity (millicurie (mCi)) at time of scan.

Ex vivo Biodistribution: All animals were sacrificed at 3 hours post [$^{18}$F]JW199 injection and organs and tumors were immediately harvested. All tissues were weighed, and radioactivity was counted using a Cobra II Geiger counter (PerkinElmer, Waltham, Massachusetts, United States of America) calibrated for [$^{18}$F] energy. The concentration of radioactivity in tumor, organs, and tissues was determined as percentage of injected dose per cubic centimeter of tissue (% ID/cc).

In vivo tumor models: For subcutaneous tumor models, human breast cancer xenografts were established by transplanting MDA-MB231 cancer cell lines ectopically into the right shoulder of female Athymic nude mice. Briefly, cultured MDA-MB231 cells were washed two times with PBS, trypsinized, and harvested in serum-containing medium. The harvested cells were then washed twice with serum-free medium and resuspended at a concentration of 2.5×106 cell/L in PBS. 100 μL of this cell suspension was injected per mouse. Tumor growth was measured every 3 days with calipers until they reached a volume of about 150 mm$^3$, which took an average of 30 days. Tumor-bearing mice were then subjected to [$^{18}$F]JW199 dosing and PET/CT imaging, as described above.

NCEH1 Measurement in Fractionated Tumor Xenograft Proteomes: MDA-MB-231 xenograft tumors were dissected after PET imaging. The edge of the tumor tissue was carefully separated from the inner portion, resulting in paired 'edge' and 'inside' tissue fractions. Tissue samples were Dounce-homogenized in PBS, then centrifuged at 4000×g for 5 min at 4° C. to remove lipids and non-lysed tissue. Membrane proteome fractions were prepared by ultracentrifugation as described above. Protein concentrations were determined via bioinchoninic acid (BCA) assay, and normalized across all samples to 1 mg/ml. 50 μL of each lysate sample was treated with 2 μM of the family-wide serine hydrolase probe, fluorophosphonate-biotin (FP-bio), at room temperature for 30 min, followed by removal of excess probe with Zeba spin columns (Thermo Fisher Scientific, Waltham, Massachusetts, United States of America). Lysate concentrations were quantified again by BCA assay, and soluble activity-dependent proximity ligation (sADPL) profiling of NCEH1 was conducted for two proteome concentrations per sample: 0.037 mg/ml and 0.012 mg/ml. Lysates were incubated with PEG-8000 at a final concentration of 5% at 4° C. for 30 min, and centrifuged at 4,000 rpm for 20 min to remove any potential assay interferences. 2 μL of each proteome sample was added to 2 μL of sADPL reagent mix, resulting in a final concentration of 200 μM of anti-NCEH1-oligonucleotide (α-NCEH1-oligo) and 4 nM of streptavidin-oligonucleotide (SA-oligo) in PBS (pH 7.2), containing 20 μg/mL poly-A, 2 mM EDTA, 1% BSA, and 0.05% goat IgG. The resulting mixture was incubated at 37° C. for 90 minutes. Ligations were performed by adding 116 μL ligation solution containing 100 nM splint oligonucleotide, 2.5 units of ampligase, 0.3 mM NAD+, 10 mM DTT, 20 mM Tris-HCl pH 8.3, 50 mM KCl and 1.5 mM MgCl$^2$. Ligation proceeded at 30° C. for 15 minutes and was terminated by adding 2.5 μL of the 10-fold dilution of the Uracil-specific excision reagent (USER) enzyme for 15 minutes at the same temperature. Ligated amplicons were pre-amplified by combining 5 μL of the final ligation mixture with 20 μL of 1.25×PCR solution and 100 nM primers and amplifying for 18 cycles. The pre-amplified solution was then diluted with 75 μL of 1×TE buffer prior to real-time, quantitative PCR (qPCR). 9 μL of the diluted solution was added to 11 μL of qPCR mix resulting in final concentrations of 0.5 μM primers and 0.25 μM Taqman probe. Samples were run on a CFX384 Real-Time PCR Detection System (Bio-Rad, Hercules, California, United States of America). Following acquisition of the raw threshold cycle count (CT) values, the relative activity fold-change was calculated by normalization with the xenograft-paired 'edge' sample using a standard amplification factor of 1.91, which was determined by a standard dilution curve in previous qPCR experiments.

The α-NCEH1-oligo and SA-oligo conjugates were prepared according to a previously published procedure[23] with the following oligo sequences:

```
α-NCEH1-oligo:
                                (SEQ ID NO: 1)
5'-amine-CATCGCCCTGGACTAGCATACCCATGAACACAAG-

TTGCGTCACGATGAGACTGGATGAA-3';

SA-oligo:
                                (SEQ ID NO: 2)
5'-OPO3-TCACGGTAGCATAAGGTGCACGTTACCTTGATTCCCG- TCC-amine-3';

splint oligo:
                                (SEQ ID NO: 3)
5'-AUAGCUACCGUGAUUCAUCCAGTGAG-3';

forward primer:
                                (SEQ ID NO: 4)
5'-ACCCATGAACACAAGTTGCG -3';

reverse primer:
                                (SEQ ID NO: 5)
5'-GGACGGGAATCAAGGTAACG-3';
and taqman probe:
                                (SEQ ID NO: 6)
5'-6-FAM-TGGATGAAT/ZEN/CACGGTAGCATAAGGTGCA- IABkFQ-3'
```

Immunoblotting: Edge and inside tumor proteomes were prepared as described above. Protein concentrations were normalized across samples to 1 mg/mL in PBS (pH 7.4, 30 μL total volume), combined with 10 μL 4×SDS-PAGE loading buffer, and boiled at 95° C. for 5 minutes. After cooling to room temperature, samples were resolved on gels sold under the tradename NUPAGE™ Novex 4-12% Bis-Tris Protein Gels (Invitrogen, Carlsbad, California, United States of America), and transferred onto nitrocellulose membranes. Membranes were blocked in 2% BSA in TBS containing 0.1% Tween-20 (TBST) and probed with primary and secondary antibodies. Primary antibodies used in this study: anti-NCEH1 (in-house mouse polyclonal 1:2000 from 1 mg/mL stock), rabbit anti-GAPDH (1:2000, Cell Signaling Technology, Danvers, Massachusetts, United States of America; #2118S). Blots were imaged on an imaging system sold under the brandname Odyssey® CLx Imager (LI-COR Biosciences, Lincoln, Nebraska, United States of America) following incubation with the fluorescence-labeled secondary antibodies sold under the names IRDye® 800CW anti-rabbit (LI-COR Biosciences, Lincoln, Nebraska, United States of America; #926-32213) or IRDye®680RD anti-mouse (LI-COR Biosciences, Lincoln, Nebraska, United States of America, #926-68072). Densitometric quantification of band intensities was performed using ImageJ software (NIH, Bethesda, Maryland, United States of America).

Immunofluorescence Imaging: Immediately following PET imaging, MDA-MB231 xenograft tumors were dissected and frozen. A portion of each tumor was embedded in optimal cutting temperature (OCT) compounds, serially sectioned at a thickness of 5 μm, and thaw-mounted onto glass slides. Slides were stored at −80° C. Frozen slides were thawed for 20 minutes at room temperature and the tissue was fixed in prechilled acetone at 4° C. for 10 minutes. Slides were air-dried for 20 minutes at room temperature, and rehydrated in 3×5 minutes PBS washes on an orbital shaker. Tissue boundaries were delineated with a hydrophobic barrier pen. Tissues were then blocked for 1 hour in 10% normal goat serum in PBST, followed by incubation with 10 μg/ml anti-NCEH1 antibody in 10% goat serum at 4° C. overnight. Slides were washed in PBST three times for 5 minutes each with gentle orbital shaking and incubated with 20 μg/ml anti-mouse-Alexa555 for 2 hours in the dark at room temperature. To visualize nuclei, 5 μg/ml DAPI was included in the secondary antibody incubation. Slides were then washed with PBST three times for 5 minutes each, dried at room temperature, coverslipped with 50 μL anti-fade mounting solution (Life Technologies, Carlsbad, California, United States of America), and sealed with nail polish. A Leica SP8 laser scanning confocal (Leica Camera LC, Wetzler, Germany) was used to image a single focal plane. Signal location was determined using HyD detectors. Post-acquisition processing was performed using ImageJ software (NIH, Bethesda, Maryland, United States of America).

Example 3

Tumor Imaging Using Radiolabeled JW199

Disclosed herein is the development of an $^{18}$F-labeled, activity-based small molecule probe targeting the cancer-associated serine hydrolase NCEH1. A focused medicinal chemistry campaign was undertaken to simultaneously preserve potent and specific NCEH1 labeling in live cells and animals, while permitting facile $^{18}$F radionuclide incorporation required for PET imaging. The resulting molecule, [$^{18}$F]JW199, labels active NCEH1 in live cells at nM concentrations and greater than 1,000-fold selectivity relative to other serine hydrolases. [$^{18}$F]JW199 displays rapid, NCEH1-dependent accumulation in mouse tissues. Finally, it is demonstrated that [$^{18}$F]JW199 labels aggressive cancer tumor cells in vivo, which uncovered localized NCEH1 activity at the leading edge of triple-negative breast cancer tumors, suggesting roles for NCEH1 in tumor aggressiveness and metastasis. More generally, these data support the broader development of potent and specific covalent PET probes to visualize localized, active enzymes in live animals.

Elevation of NCEH1 mRNA, protein abundance, and activity has been observed in a range of aggressive human cancer cell lines and primary tumors.[17-19] NCEH1 regulates levels of neutral ether lipids and cholesterol esters, but it remains unclear how these metabolites are involved in aggressive cancer cell phenotypes.[17, 20] Nonetheless, the consistent and dramatic upregulation of NCEH1 activity in multiple aggressive cancer cells suggests: 1) it is involved in or associated with general processes of tumor progression; 2) its activity may serve as a marker for malignant potential. Thus, there is an interest in visualizing this enzyme in cells, tissues, live animals and potentially human patients. Potent, selective, and activity-dependent covalent inhibitors of NCEH1 have been reported, including a fluorescent probe capable of labeling active NCEH1 in cell culture.[21] However, none of these scaffolds permit in vivo imaging, which would be necessary for studying this enzyme in the tumor microenvironment and for potential diagnostic applications.

Figure 5B:
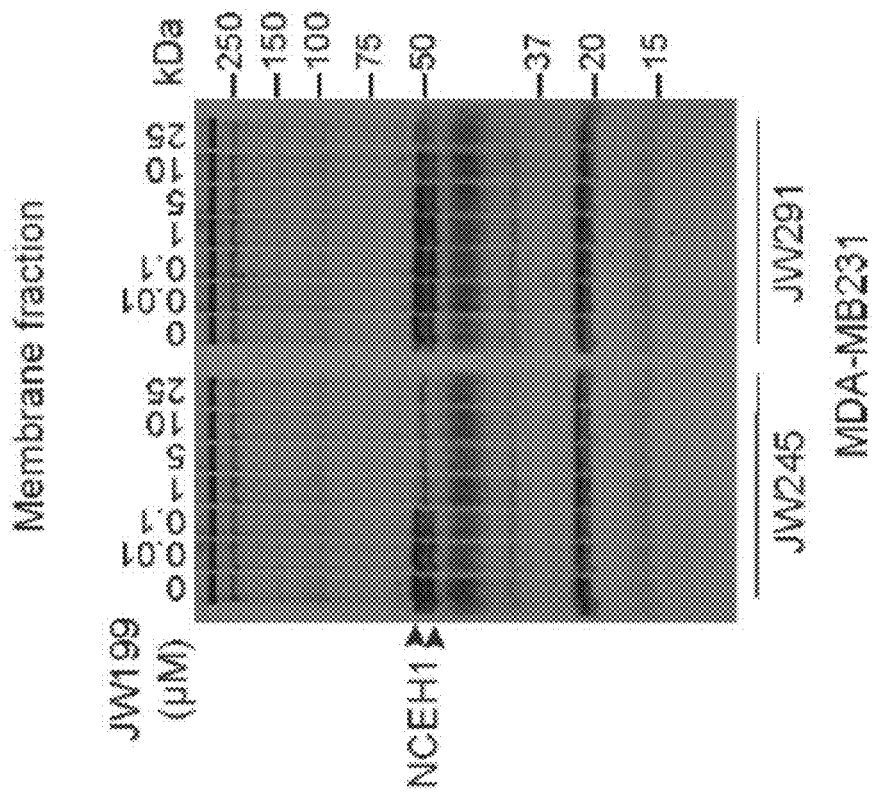
FIGS. 5A and 5B: Additional exemplary inhibitors of neutral cholesterol ester hydrolase 1 (NCEH1).
Figure 5A:
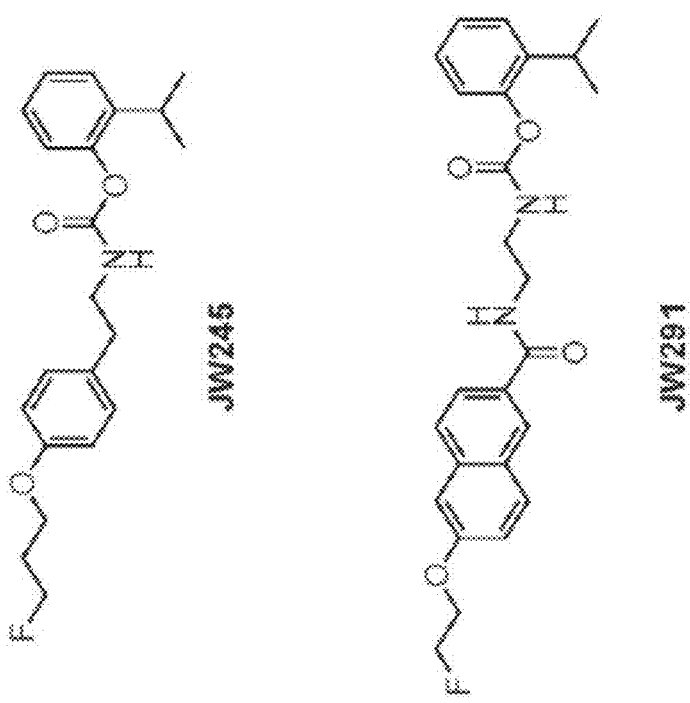
Figure 6B:
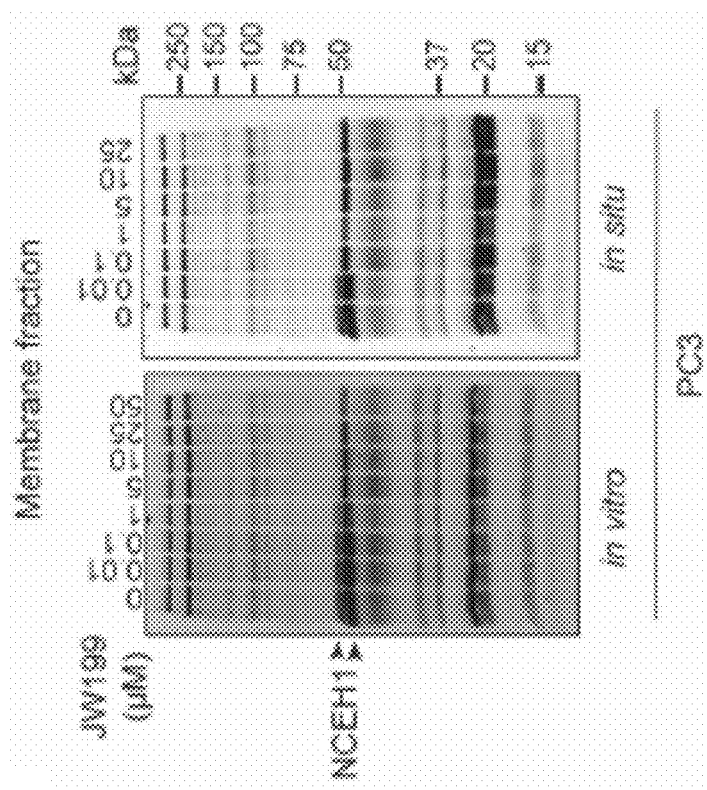
FIGS. 6A-6D: Activity-based protein profiling (ABPP) of serine hydrolase activity in two different model cancer cell lines.
Figure 6A:
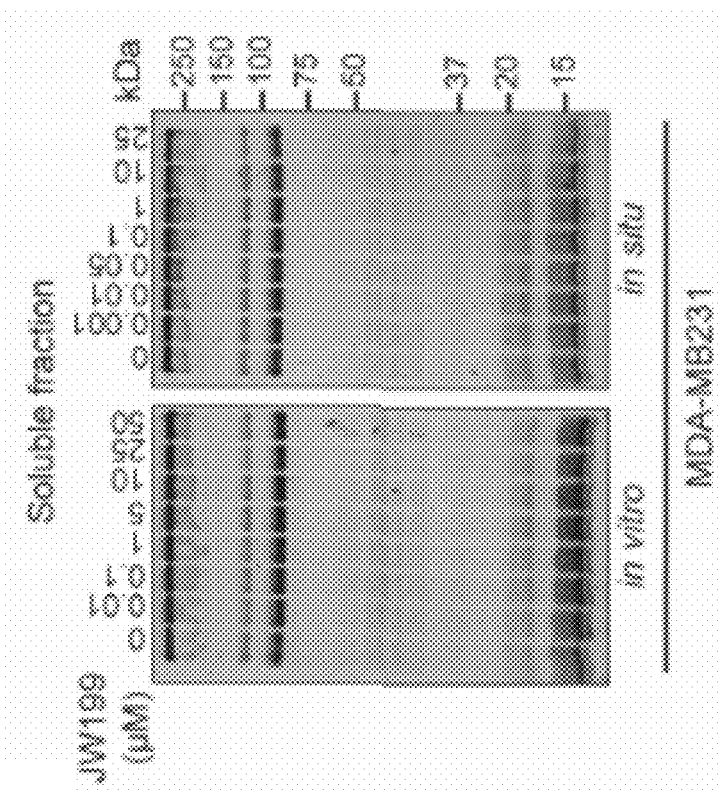
Figure 6D:
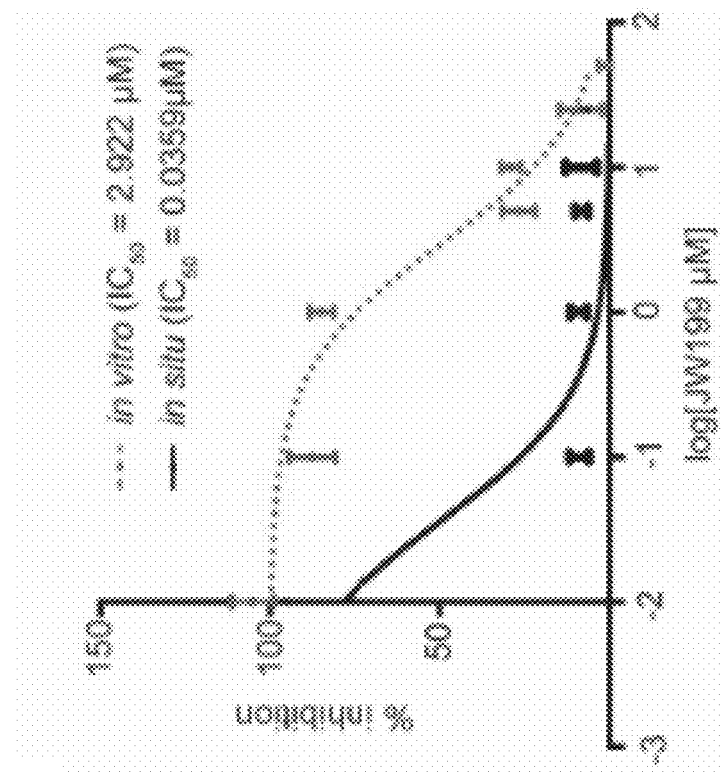
Figure 6C:
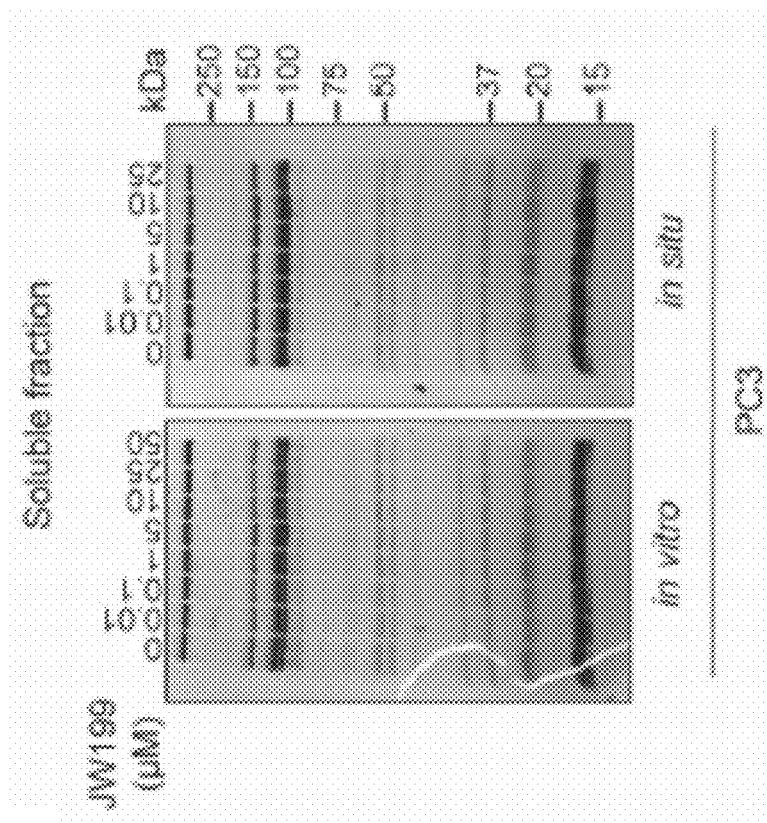
Figure 7:
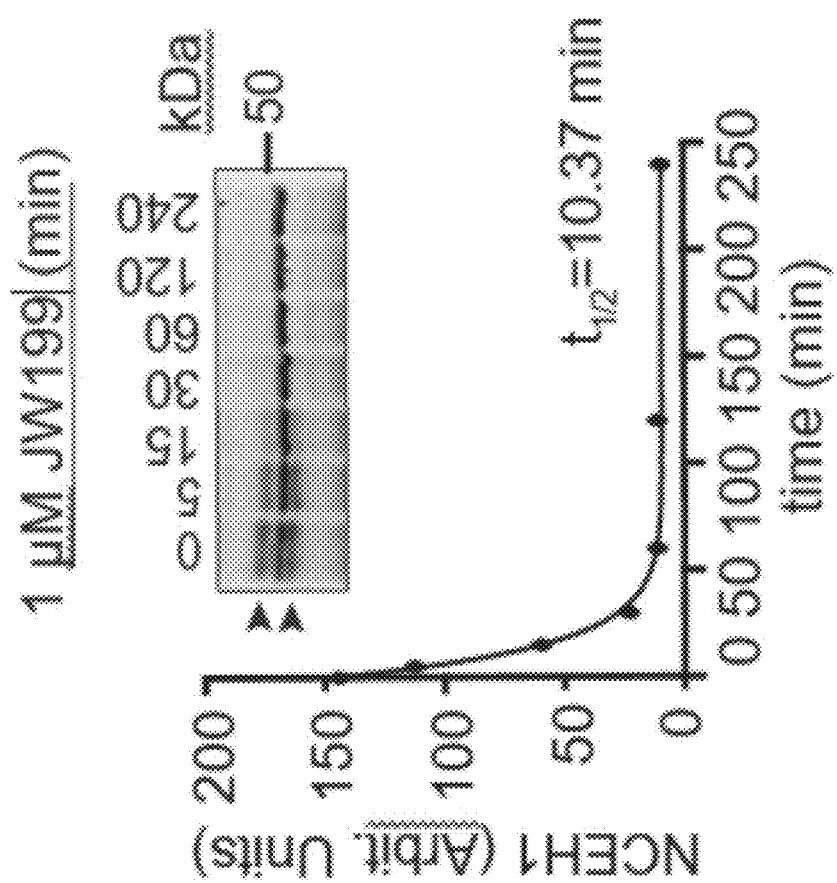
FIG. 7 is a graph showing time-dependent inhibition of neutral cholesterol ester hydrolase 1 (NCEH1) by 2-isopropylphenyl-(4-(2-fluoroethoxy)phenethyl)carbamate (JW199; 1 micromolar (µM)) in live PC3 prostate cancer cells. Quantification of band intensities (Arbitrary Units) was performed with ImageJ software and were fit to a single-phase exponential decay model. The inset gel image is representative of n=3 independent experiments.

A focused series of carbamate-based small molecules was synthesized and screened. Compounds were designed that can retain solubility, cellular and in vivo activity, and NCEH1-target potency and specificity, and a latent synthon for radionuclide incorporation. See FIG. 5A. For the latter attribute, $^{18}$F-compatible synthons were planned for in the aromatic/hydrophobic carbamoylating portion of the inhibitor. All three lead compounds displayed good selectivity for NCEH1, but two molecules (JW245 and JW291) were less potent against NCEH1 compared to JW199. See FIGS. 1A, 4, 5A, and 5B. Family-wide profiling of serine hydrolases in two aggressive cancer cell lines (MDA-MB231 and PC3) confirmed potent inhibition of NCEH1 in live cells by JW199 ($IC_{50}$ values in the low nM range) that was >1,000-fold more selective over other detected serine hydrolase targets. See FIGS. 1B, 1C, and 6A-6D. Though comparably selective, JW199 was less potent in in vitro lysate profiling, underscoring the importance of live cell profiling to fully ascertain compound targeting landscapes. Kinetic profiling in live cells demonstrated rapid labeling of NCEH1, saturating within ~20 minutes (t½=10.37 min). See FIG. 7. These properties, taken together, prompted further development of a radiosynthetic route to generate $^{18}$F-labeled JW199 for in vivo PET imaging.

Figure 1D:
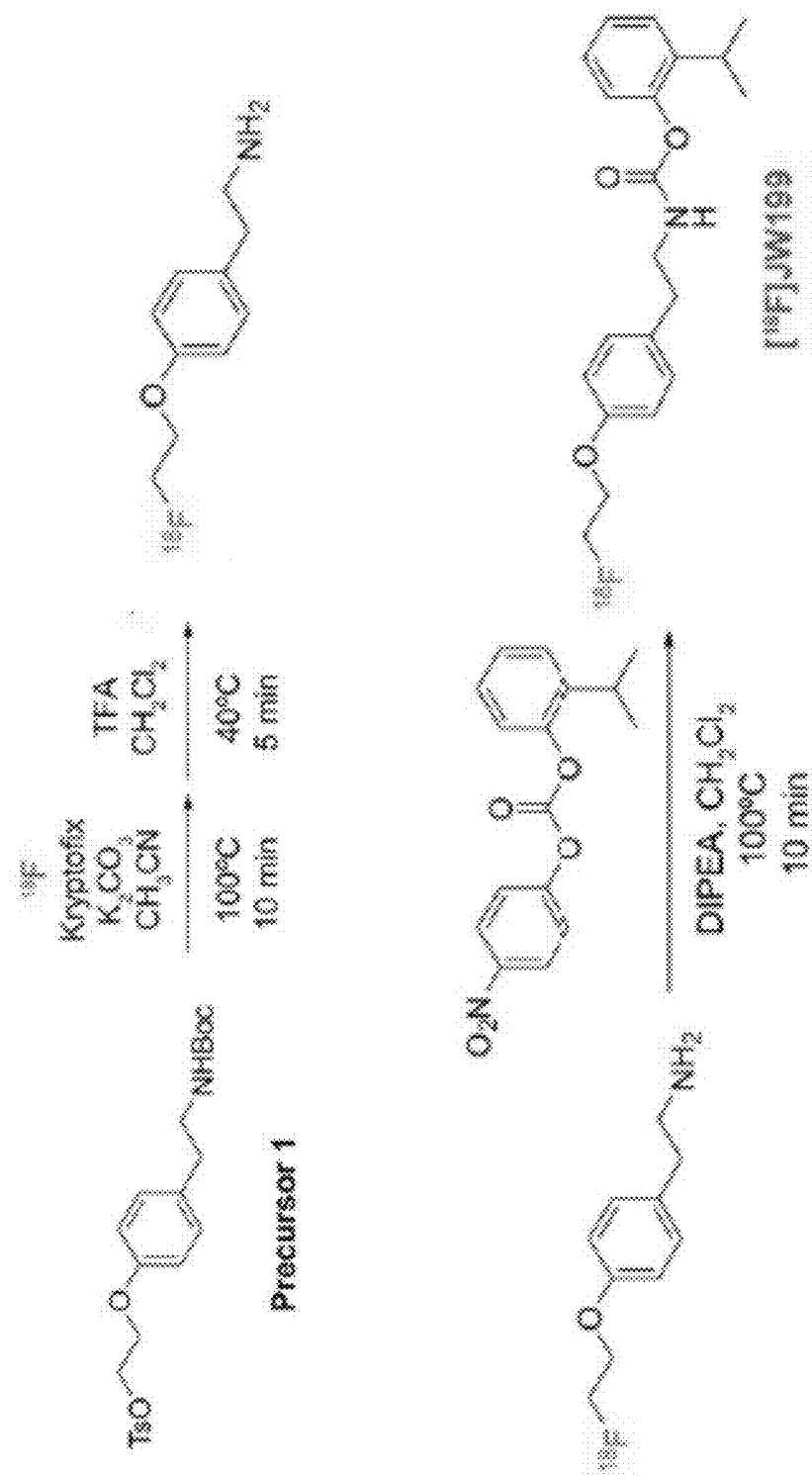

Radiosynthetic strategies generally install $^{18}$F in the final step of synthesis due to its short half-life of 109.8 minutes. Strategies were considered that were amenable to installation of a suitable electrophilic group at the 2-phenoxyethyl position in the elaborated carbamate structure, or installation of $^{18}$F on an earlier precursor followed by rapid construction of the molecule. Iterative rounds of synthesis ultimately identified a route that took the latter approach: incorporating $^{18}$F into JW199 using an N-Boc-phenoxyethyltosyl precursor 1 (see FIG. 1D and FIG. 4) to directly fluorinate the inhibitor scaffold via nucleophilic substitution facilitated by a tosylate leaving group.[22] This was accomplished by automated radiolabeling of precursor 1 with aqueous [$^{18}$F]F-(4, 750±50 mCi, n=15) and $K_2CO_3$ in acetonitrile, followed by rapid, quantitative removal of the Boc protecting group using trifluoroacetic acid (TFA). The resulting $^{18}$F-labelled compound (2) was reacted with an activated carbonate, yielding [$^{18}$F]JW199. See FIGS. 1D and 1E. [$^{18}$F]JW199 was purified via semi-preparative HPLC, and the identity of the new radiotracer was confirmed via HPLC and co-injection with a cold (i.e., non-radiolabeled) JW199 standard. See FIG. 1E. Notably, the in situ, automated, one-pot and multistep synthetic route facilitates [$^{18}$F]JW199 radiosynthesis (35 min) and purification (30 min) in total<65 minutes. See FIGS. 1D and 1E. This route results in consistent radiochemical yields (4±0.5% decay corrected radiosynthetic yield, n=15), specific radioactivity (500-510 GBq/μmol) and purity (99±1%, n=15) that are comparable to optimized radiosyntheses for preclinical and clinical radiotracers. The resulting [$^{18}$F]JW199 was chemically stable in physiologic buffers, consistent with the non-labile C—F bond. See FIG. 1F.

Figure 2E:
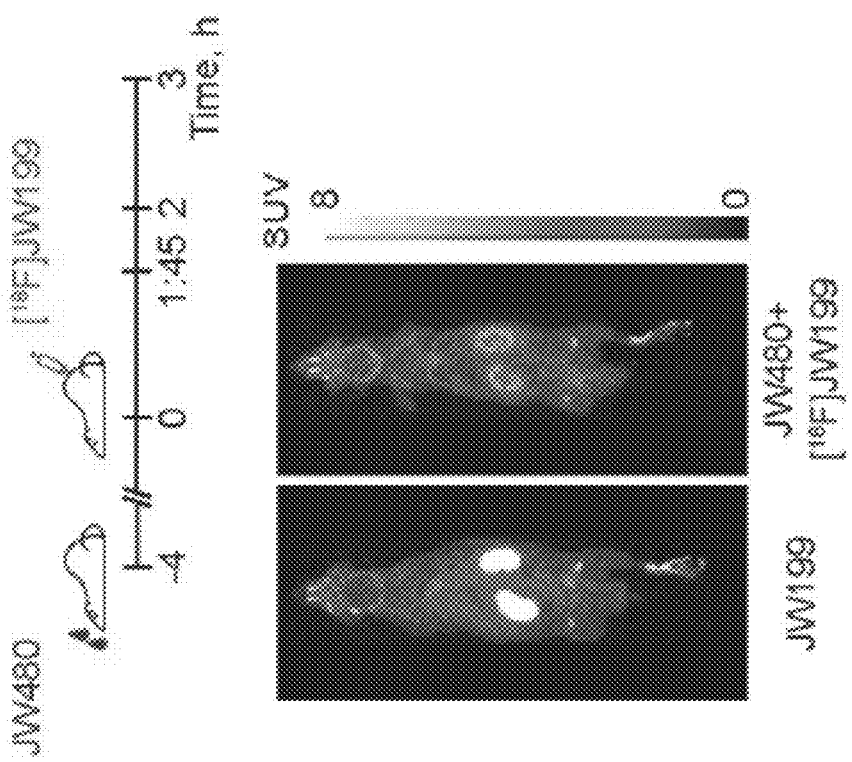
Figure 2D:
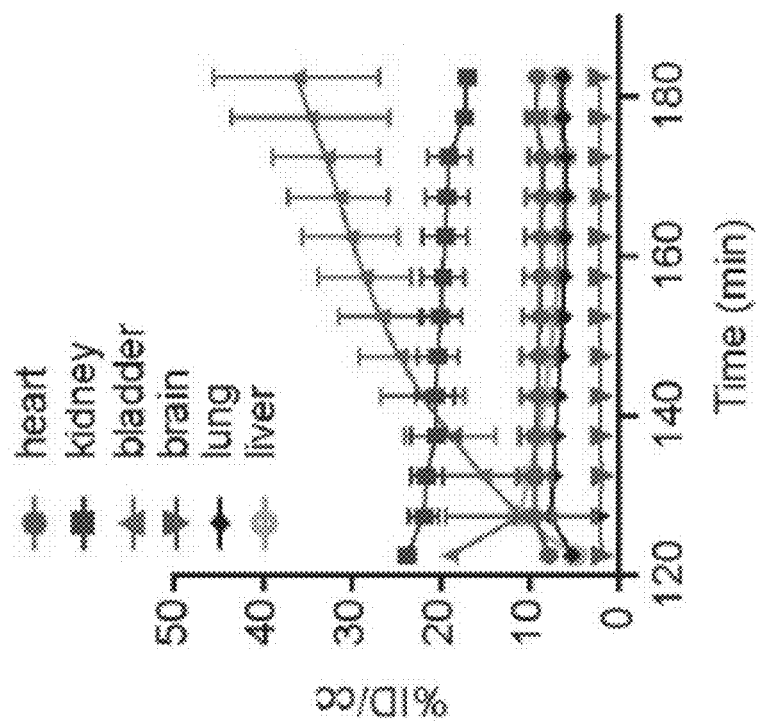
Figure 8:
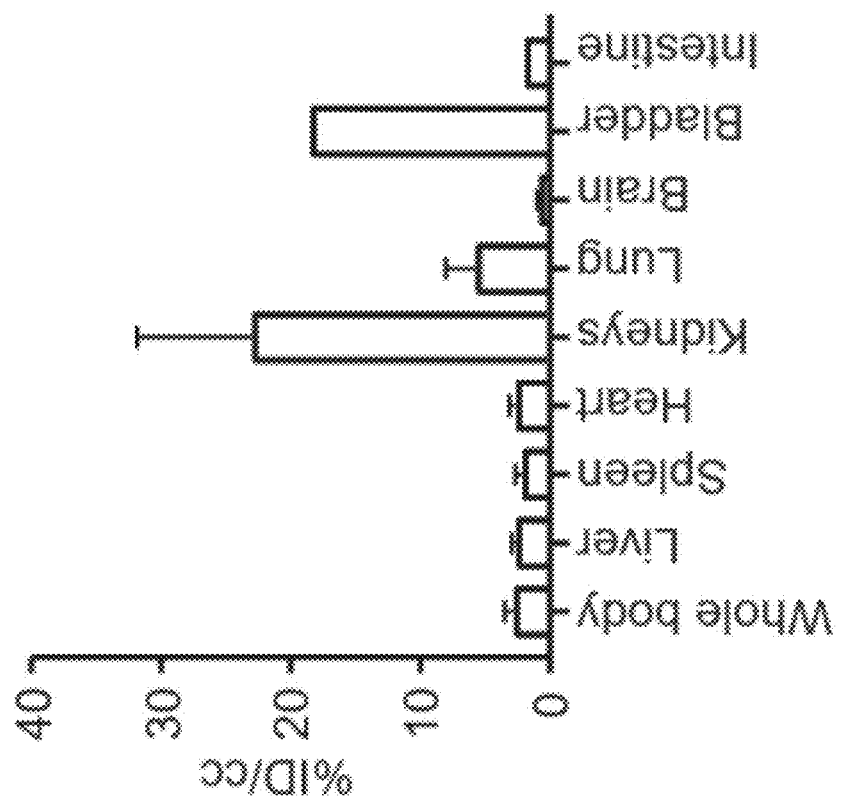
FIG. 8 is a graph showing the ex vivo biodistribution of fluorine-18-labeled 2-isopropylphenyl-(4-(2-fluoroethoxy) phenethyl)carbamate ([$^{18}$F]JW199). Quantification of radiotracer signal in the indicated tissues 3 hours after injection of 150 microcuries (µCi) of [$^{18}$F]JW199. Data are means percentage injected dose per cubic centimeter (% ID/cc)±standard deviation (SD) (n=3 male mice). Although this time point differs from the imaging experiment, the same general trends are observed.

To test the utility of [$^{18}$F]JW199 in visualizing active NCEH1 via PET imaging, nude mice were treated with [$^{18}$F]JW199 (~100 μCi) intravenously (i.v.). After allowing stable distribution, the inventors conducted whole body X-ray computed tomography (CT) with subsequent PET imaging (see FIG. 2A) and assessed [$^{18}$F]JW199 biodistribution. Significant signal accumulation was observed in tissues like kidney, heart and lung, which have relatively high Nceh1 expression in mice. See FIGS. 2B, 2C, and FIG. 8 (mRNA levels obtained from BioGPS.org). By contrast, relatively low uptake was observed in tissues with low Nceh1 mRNA levels such as adipose depots, liver, and bone. A low PET signal was observed in the brain despite relatively high levels of active NCEH1 in this tissue, consistent with low CNS penetration. Ex vivo quantification of whole tissue radioactivity corroborated the biodistribution pattern observed by PET imaging. See FIG. 8. PET signal in target organs quickly reached and maintained constant levels during the entire imaging procedure. See FIG. 2D.

Figure 2F:
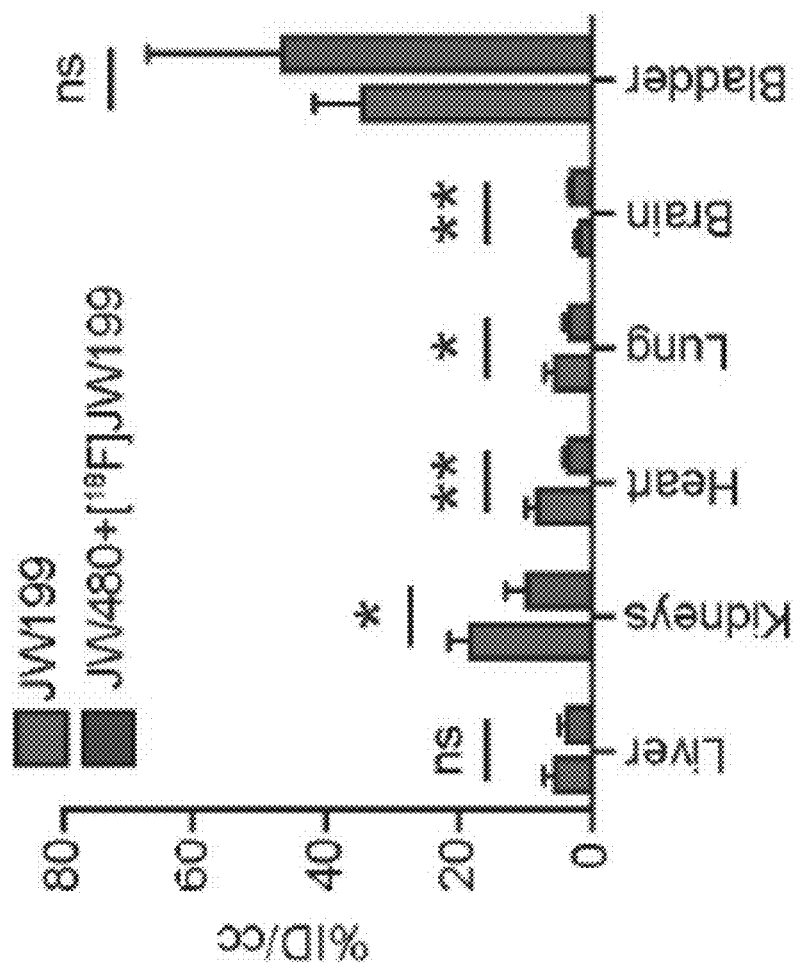
Figure 9B:
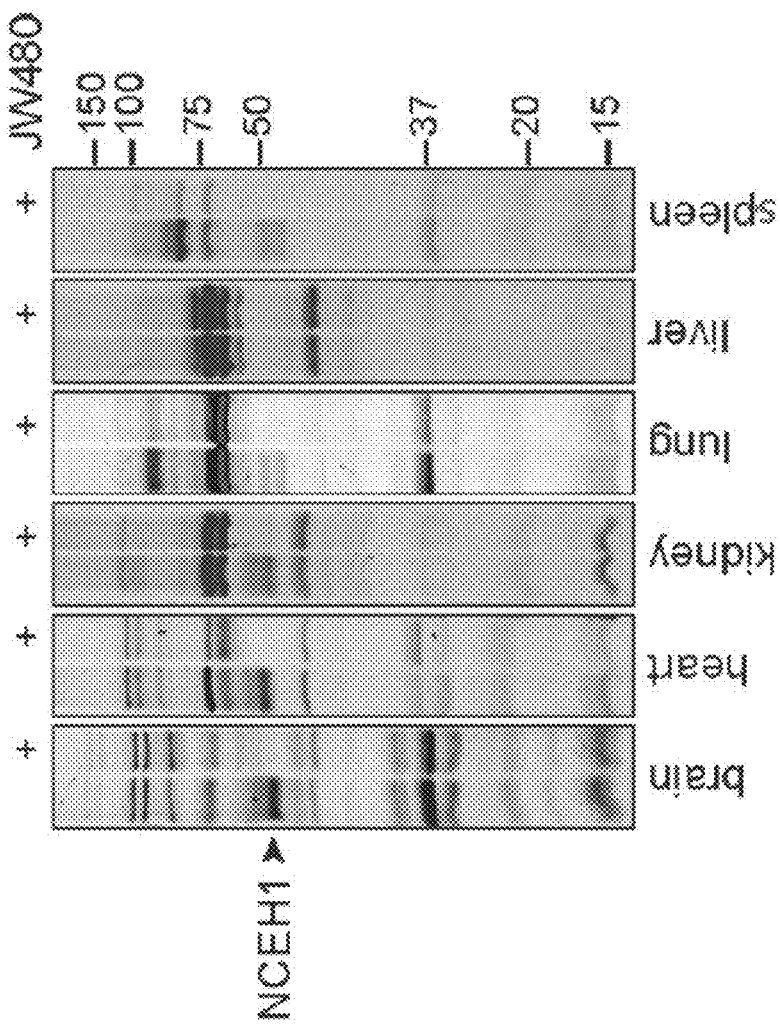
FIGS. 9A and 9B: Gel-based competitive activity-based protein profiling (ABPP) profiles of several murine membrane proteomes following treatment with fluorine-18-labeled 2-isopropylphenyl-(4-(2-fluoroethoxy)phenethyl)carbamate ([$^{18}$F]JW199) with and without 2-isopropylphenyl)-(2-(naphthalen-2-yl)ethyl)carbamate (JW480; 80 milligrams per kilogram (mg/kg)).
Figure 9A:
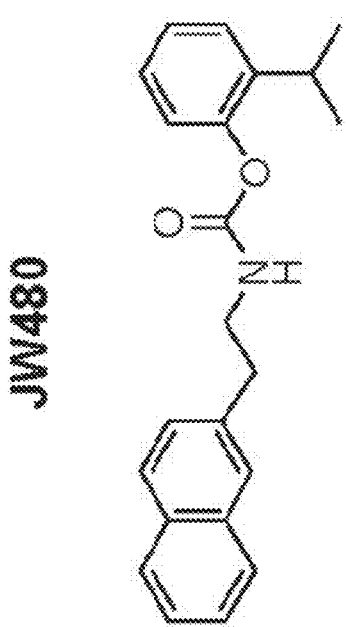

To directly verify target-specific accumulation in vivo, a competition experiment was performed with a non-radioactive inhibitor of NCEH1, JW480.[18] See FIG. 9A. Pretreatment of mice with JW480 followed by [$^{18}$F]JW199 administration resulted in significantly diminished radiotracer signal in the heart, lung, and kidney. See FIGS. 2E and 2F. Intriguingly, JW480 pre-treated mice also displayed slightly elevated radioactivity in urine and brain, suggesting that competition for enzymatic engagement can increase the likelihood of radiotracer accumulation in tissues with either low pharmacologic access (e.g., brain) or relative NCEH1 abundance. Gel-based profiling of serine hydrolase activity in these tissues confirmed specific and significant inhibition of NCEH1 in JW480 pre-treated mice. See FIG. 9B. Together, these data confirmed target labeling and retention in NCEH1-positive cells, which could provide differential imaging opportunities relative to reversible radiotracers.

Figure 3B:
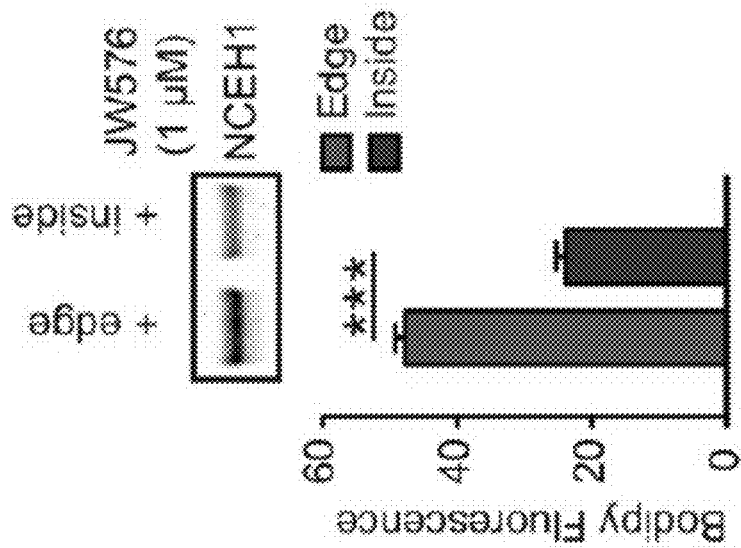
FIGS. 3A-3E: [$^{18}$F]JW199-mediated labeling of breast cancer tumor xenografts in vivo.
Figure 3A:
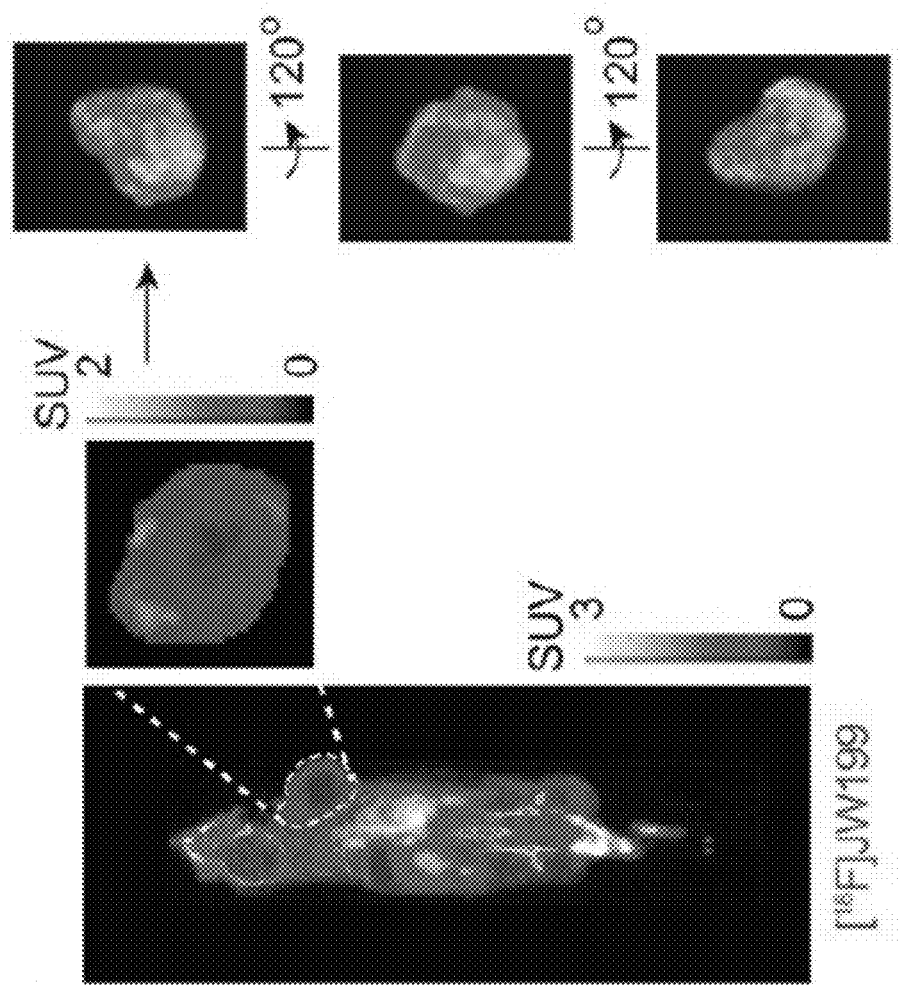
Figure 10:
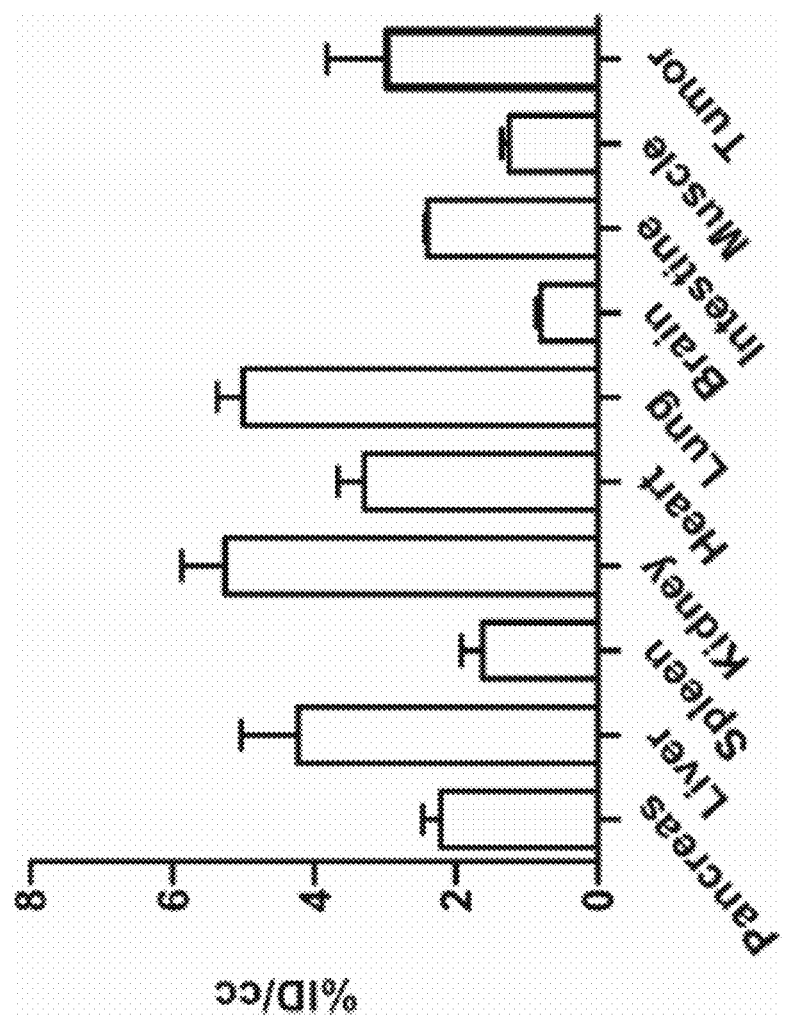
FIG. 10 is a graph showing ex vivo biodistribution of fluorine-18-labeled 2-isopropylphenyl-(4-(2-fluoroethoxy) phenethyl)carbamate ([$^{18}$F]JW199) radiotracer in mice bearing MDA-MB231 breast cancer cell xenografts. Quantification of radiotracer signal in the indicated tissues 3 hours after injection of 150 microcuries (µCi) of radiotracer. Data are means of percentage injected dose per cubic centimeter (% ID/cc)±standard deviation (SD) (n=3 female mice). Note that although this time point differs from the imaging experiment, the same general trends are observed.
Figure 12B:
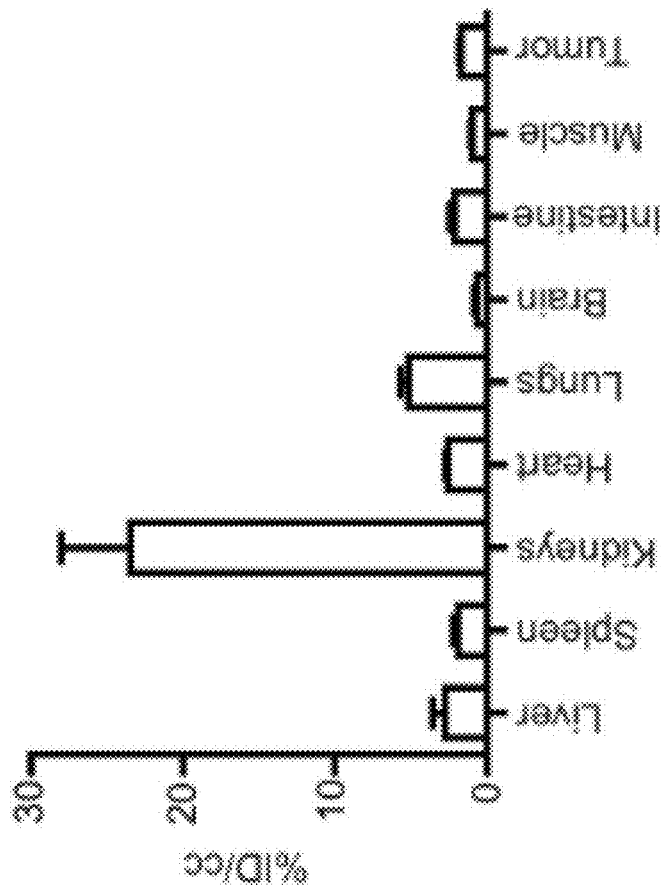
FIGS. 12A-12C: In vivo prostate cancer tumor images with fluorine-18-labeled 2-isopropylphenyl-(4-(2-fluorethoxy)phenethyl)carbamate ([$^{18}$F]JW199) tracer.
Figure 12A:
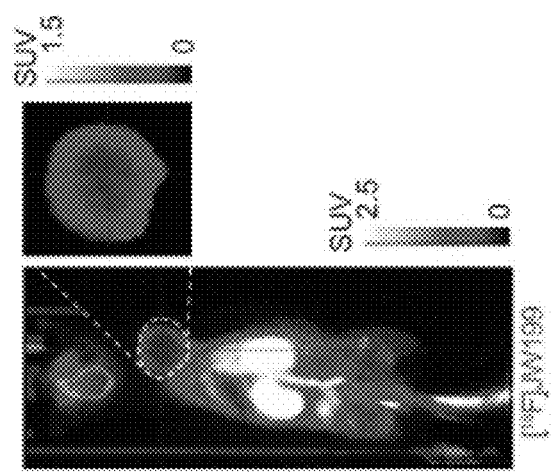
Figure 12C:
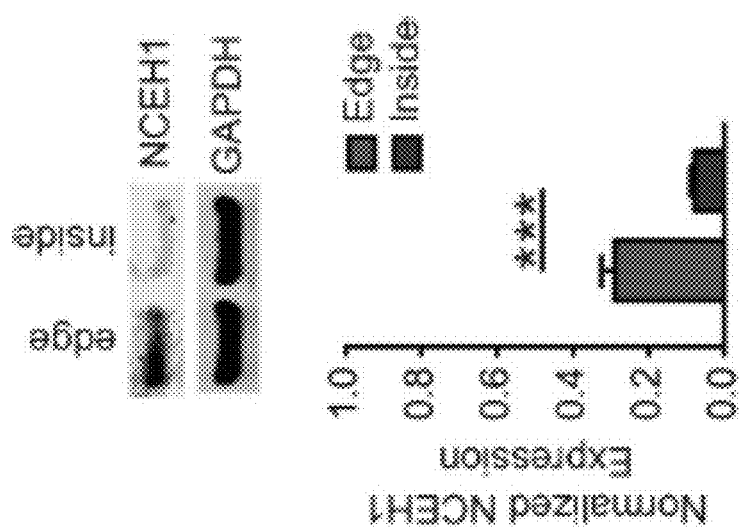

Since NCEH1 is elevated in many aggressive cancer cells, it was reasoned that imaging NCEH1 could allow for detection and tracking of malignant tumor cells in vivo. To test this, the subcutaneous MDA-MB231 human breast cancer xenografts—a cell line with relatively high levels of active NCEH1—were established in nude female mice. Once the tumors reached ~150-180 mm$^3$, 150 μCi of [$^{18}$F] JW199 was administered i.v., and dynamic PET/CT imaging was performed. A similar PET signal and biodistribution profile was observed as in non-tumor bearing mice, as well as radiotracer accumulation in breast tumor xenograft cells. See FIGS. 3A and 10. Intriguingly, the marked heterogeneity within tumors was observed, with the highest PET signal relegated to cells on the outer edge of the tumors. See FIG. 3A. This distribution was independent of tumor size, and notably absent in other target tissues, suggesting that it was unique to the xenografts and/or tumor cells. To determine whether this pattern reproduced in other tumor types, the same experiment was performed in mice bearing PC3 prostate cancer xenografts. [$^{18}$F]JW199 treatment likewise resulted in enhanced labeling of the tumor boundary in PC3 xenografts. See FIGS. 12A-12C. Even with the heterogeneous signal distribution observed in tumors, ex vivo quantitation revealed that higher total radioactivity was present in bulk tumor tissue relative to surrounding muscle in both breast and prostate cancer models, which collectively enabled direct visualization of tumor boundaries. See FIGS. 3A, 10, and 12A-12C.

Figure 3E:
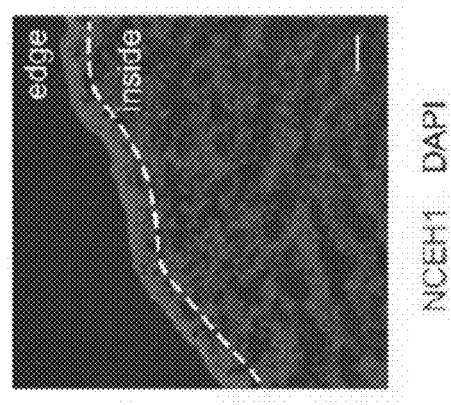
Figure 3D:
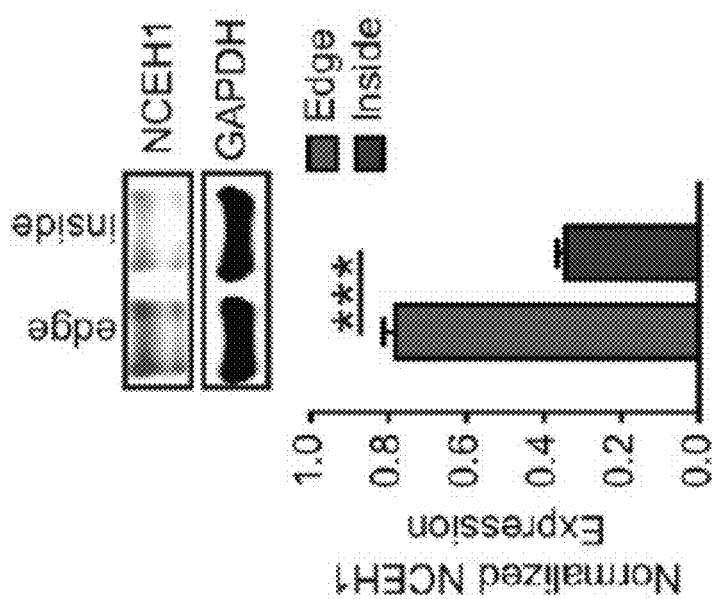
Figure 3C:
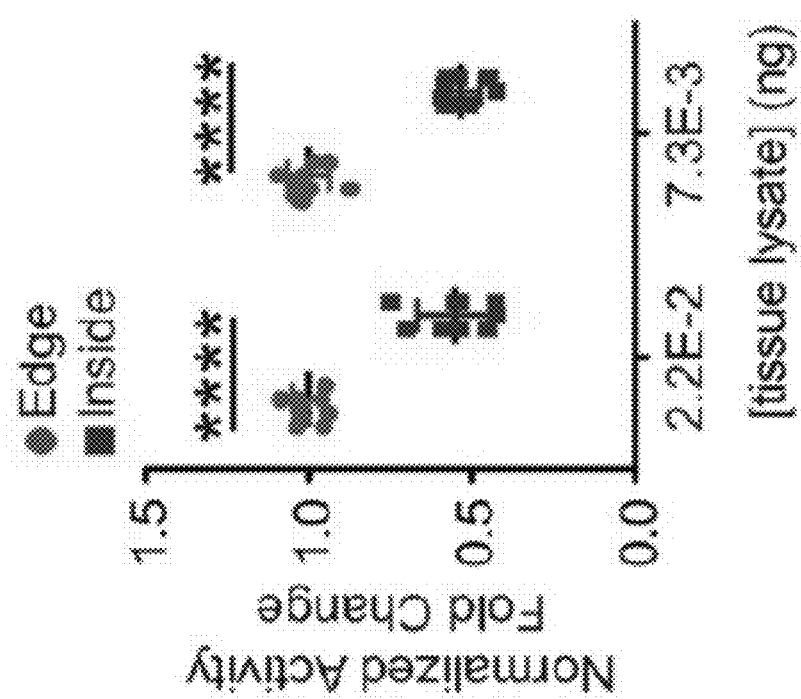
Figure 11:
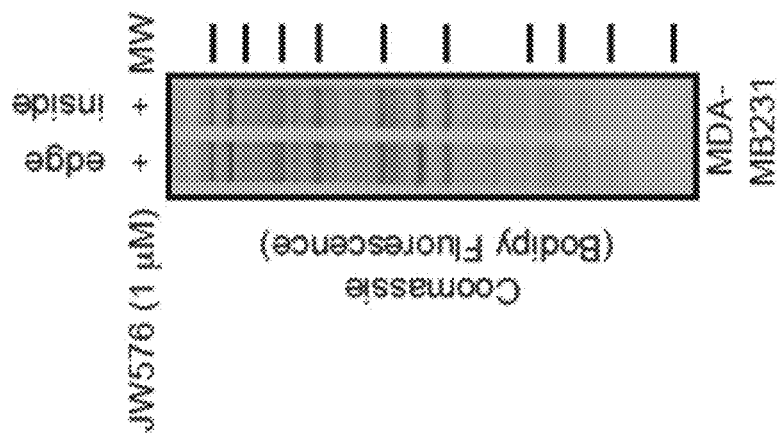
FIG. 11 is an image of coomassie staining of activity-based protein profiling (ABPP) gels as described for FIG. 3B demonstrating equal loading of lysates between sample lanes.

To determine if the heterogenous PET pattern observed in tumors was due to differential NCEH1 activity and/or expression throughout the tumor, NCEH1 protein abundance and activity was quantified in distinct tumor regions with several orthogonal methods. Gel-based measurements of active enzyme in microdissected tumor cells from the edge and core of xenografts were made using a specific fluorescent probe that labels active NCEH1, JW576,[21] which confirmed significantly higher NCEH1 activity in cells isolated from the edge of MDA-MB231 xenografts. See FIGS. 3B and 11. This difference in active NCEH1 was also confirmed using a more sensitive method, soluble activity-dependent proximity ligation.[23, 24] See FIG. 3C. Activity-dependent proximity ligation has been reported in PCT/US18/62231 (International Publication No. WO 2019/104155) which is incorporated by reference herein in its entirety. Likewise, Western blot detection of NCEH1 revealed reduced abundance in the tumor core relative to the edge of both MDA-MB231 and PC3 xenografts. See FIGS. 3D and 12C. Finally, immunofluorescent imaging of whole xenograft tissue sections confirmed NCEH1 localization along the outer edges of the tumor, with comparatively little NCEH1 observed within the tumor, reinforcing the microenvironmental heterogeneity observed via PET imaging with [$^{18}$F]JW199. See FIG. 3E. Taken together, these results not only validate the utility of [$^{18}$F]JW199 as a robust and specific PET-compatible radiotracer, but also suggest that NCEH1-mediated signaling varies within the tumor microenvironment.

Here is described development of a potent and selective PET radiotracer for an intracellular enzyme by activity-based covalent modification of an active site nucleophile. By balancing proteome-wide target engagement profiling, physicochemical properties, and demanding radiosynthetic processes, a first-in-class activity-based PET probe is described to specifically image active NCEH1 in both wild-type and tumor-bearing mice. Using [$^{18}$F]JW199 to detect malignant MDA-MB231 triple negative breast cancer cells in vivo, substantial intratumor heterogeneity in NCEH1 protein abundance and activity was discovered. These insights, which would not be possible with in vitro cellular models, raise intriguing hypotheses about the role of NCEH1 in tumor progression and metastasis.

For example, without being bound to any one theory, the increased NCEH1 abundance and activity at the growing edge of tumors could be related to its role in aggressive, pro-metastatic cellular processes. Spatially-restricted interaction with stromal cells or other biologic mediators could be a root cause of localized NCEH1 activity in tumors and reciprocal alteration in the phenotype of surrounding cells. Finally, these data raise the question of whether this distribution pattern is consistent from primary to metastatic tumor lesions, as the environmental and mechanical forces are unique between these populations. These questions warrant future focused studies to test the utility of [$^{18}$F]JW199 for detection of metastatic tumor lesions in vivo.

Finally, the recent resurgence of covalent small molecule chemical probes and therapeutics has established their unique capacity for increased potency, and potential specificity, relative to small molecules that bind protein targets reversibly. In particular, several studies have demonstrated that kinetic differentiation of targets can be leveraged for increased on-target in vivo activity.[25] Within this context, this study provides a methodological blueprint for the development of activity-based, covalent radiotracers for proteins involved in disease pathology.

In particular, the data suggest that potent and specific covalent radiotracers can differentiate between on- and off-target labelling through kinetic competition in vivo. This is supported by the rapid and stable signal observed in tissues with high NCEH1 activity, as well as the increased PET signal in tissues with either lower pharmacologic access and/or NCEH1 activity when NCEH1 is blocked in other tissues. Thus, tuning target potency and biodistribution properties with covalent imaging probes can provide for selectivity profiles that are unique from, and potentially superior to traditional reversible tracers. Therefore, beyond the implications for detecting and studying NCEH1 activity, this work provides additional evidence supporting the development of covalent PET probes for precision imaging of molecular signatures and activities in animals.

REFERENCES

All references listed in the instant disclosure, including but not limited to all patents, patent applications and publications thereof, scientific journal articles, and database entries (including but not limited to UniProt, EMBL, and GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

1. D. K. Nomura; M. M. Dix; B. F. Cravatt, Nat Rev Cancer 2010, 10, 630-638.
2. R. E. Moellering; B. F. Cravatt, Chem Biol 2012, 19, 11-22.
3. L. E. Sanman; M. Bogyo, Annu Rev Biochem 2014, 83, 249-273.
4. Y. Liu; M. P. Patricelli; B. F. Cravatt, Proc Natl Acad Sci USA 1999, 96, 14694-14699.
5. N. Jessani; S. Niessen; B. Q. Wei; M. Nicolau; M. Humphrey; Y. Ji; W. Han; D. Y. Noh; J. R. Yates, 3$^{rd}$; S. S. Jeffrey; B. F. Cravatt, Nat Methods 2005, 2, 691-697.
6. G. Li; J. E. Montgomery; M. A. Eckert; J. W. Chang; S. M. Tienda; E. Lengyel; R. E. Moellering, Nat Commun 2017, 8, 1775.
7. G. Blum; S. R. Mullins; K. Keren; M. Fonovic; C. Jedeszko; M. J. Rice; B. F. Sloane; M. Bogyo, Nat Chem Biol 2005, 1, 203-209.
8. J. W. Chang; A. B. Cognetta, 3$^{rd}$; M. J. Niphakis; B. F. Cravatt, ACS Chem Biol 2013, 8, 1590-1599.
9. M. D. Shults; B. Imperiali, J Am Chem Soc 2003, 125, 14248-9.
10. C. S. Lentz; J. R. Sheldon; L. A. Crawford; R. Cooper; M. Garland; M. R. Amieva; E. Weerapana; E. P. Skaar; M. Bogyo, Nat Chem Biol 2018, 14, 609-617.
11. T. H. Witney; M. L. James; B. Shen; E. Chang; C. Pohling; N. Arksey; A. Hoehne; A. Shuhendler; J. H. Park; D. Bodapati; J. Weber; G. Gowrishankar; J. Rao; F. T. Chin; S. S. Gambhir, Sci Transl Med 2015, 7, 310ra169.
12. W. Kim; T. M. Le; L. Wei; S. Poddar; J. Bazzy; X. Wang; N. T. Uong; E R. Abt; J. R. Capri; W. R. Austin; J. S. Van Valkenburgh; D. Steele; R. M. Gipson; R. Slavik; A. E. Cabebe; T. Taechariyakul; S. S. Yaghoubi; J. T. Lee; S. Sadeghi; A. Lavie; K. F. Faull; O. N. Witte; T. R. Donahue; M. E. Phelps; H. R. Herschman; K. Herrmann; J. Czemin; C. G. Radu, Proc Natl Acad Sci USA 2016, 113, 4027-4032.
13. M. Rashidian; E. J. Keliher; A. M. Bilate; J. N. Duarte; G. R. Wojtkiewicz; J. T. Jacobsen; J. Cragnolini; L. K. Swee; G. D. Victora; R. Weissleder; H. L. Ploegh, Proc Natl Acad Sci USA 2015, 112, 6146-6151.
14. C. Marcus; E. Mena; R. M. Subramaniam, Clin Nucl Med 2014, 39, e413-22.
15. Z. Chen; W. Mori; H. Fu; M. A. Schafroth; A. Hatori; T. Shao; G. Zhang; R. S. Van; Y. Zhang; K. Hu; M. Fujinaga; L. Wang; V. Belov; D. Ogasawara; P. Giffenig; X. Deng; J. Rong; Q. Yu; X. Zhang; M. I. Papisov; Y. Shao; T. L. Collier; J. A. Ma; B. F. Cravatt; L. Josephson; M. R. Zhang; S. H. Liang, J Med Chem 2019, 62, 8866-8872.
16. R. K. Muir; N. Zhao; J. Wei; Y. H. Wang; A. Moroz; Y. Huang; Y. C. Chen; R. Sriram; J. Kurhanewicz; D. Ruggero; A. R. Renslo; M. J. Evans, ACS Cent Sci 2019, 5, 727-736.
17. K. P. Chiang; S. Niessen; A. Saghatelian; B. F. Cravatt, Chem Biol 2006, 13, 1041-1050.
18. J. W. Chang; D. K. Nomura; B. F. Cravatt, Chem Biol 2011, 18, 476-84.
19. N. Jessani; Y. Liu; M. Humphrey; B. F. Cravatt, Proc Natl Acad Sci USA 2002, 99, 10335-10340.
20. H. Okazaki; M. Igarashi; M. Nishi; M. Sekiya; M. Tajima; S. Takase; M. Takanashi; K. Ohta; Y. Tamura; S. Okazaki; N. Yahagi; K. Ohashi; M. Amemiya-Kudo; Y. Nakagawa; R. Nagai; T. Kadowaki; J. Osuga; S. Ishibashi, J Biol Chem 2008, 283, 33357-33364.
21. J. W. Chang; R. E. Moellering; B. F. Cravatt, Angew Chem Int Ed Engl 2012, 51, 966-970.
22. H. M. Betts; S. Milicevic Sephton; C. Tong; R. O. Awais; P. J. Hill; A. C. Perkins; F. I. Aigbirhio, J Med Chem 2016, 59, 9422-9430.
23. G. Li; R. E. Moellering, Chembiochem 2019, 20, 1599-1605.
24. G. Li; M. A. Eckert; J. W. Chang; J. E. Montgomery; A. Chryplewicz; E. Lengyel; R. E. Moellering, Proc Natl Acad Sci USA 2019, 116, 21493-21500.
25. B. R. Lanning; L. R. Whitby; M. M. Dix; J. Douhan; A. M. Gilbert; E. C. Hett; T. O. Johnson; C. Joslyn; J. C. Kath; S. Niessen; L. R. Roberts; M. E. Schnute; C. Wang; J. J. Hulce; B. Wei; L. O. Whiteley; M. M. Hayward; B. F. Cravatt, Nat Chem Biol 2014, 10, 760-767.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A compound having a structure of the formula:

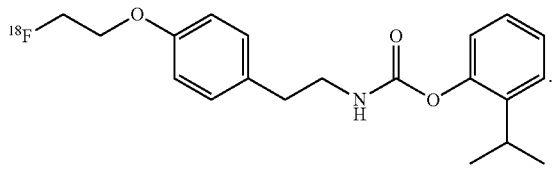 [SMILES: CC(C)c1ccccc1OC(=O)NCCc1ccc(OCC[18F])cc1]

2. A method of labeling neutral cholesterol ester hydrolase 1 (NCEH1), wherein the method comprises contacting a sample with a compound having a structure of the formula:

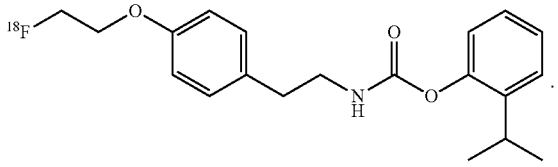 [SMILES: CC(C)c1ccccc1OC(=O)NCCc1ccc(OCC[18F])cc1]

3. The method of claim 2, wherein the sample comprises one of the group consisting of a cell, a cell culture, a tissue, an organ, and a subject.

4. A method of visualizing a tumor in a subject, wherein the method comprises:
   (a) administering to a subject having or suspected of having a tumor a tracer compound having the formula:

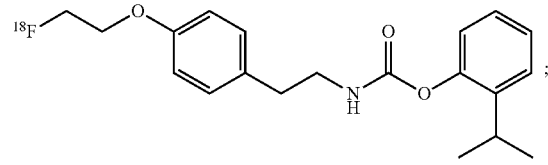 [SMILES: CC(C)c1ccccc1OC(=O)NCCc1ccc(OCC[18F])cc1]

(b) detecting radioactivity of the tracer compound, thereby visualizing a tumor or the edges thereof when a tumor is present in said subject.

5. The method of claim 4, where detecting radioactivity of the tracer compound is performed via single-photon emission computed tomography (SPECT) and/or positron emission tomography (PET).

6. The method of claim 4, wherein the subject has a tumor and the method further comprises:
   (c) administering a cancer treatment or a potential cancer treatment to the subject;
   (d) repeating steps (a) and (b), thereby re-visualizing the tumor visualized in step (b); and
   (e) comparing the tumor as visualized in step (b) to the tumor as visualized in step (d), thereby determining the in vivo effectiveness of the cancer treatment or the potential cancer treatment.

7. The method of claim 6, wherein the cancer treatment or potential cancer treatment for cancer is a pharmaceutical agent known or suspected to treat cancer.

8. The method of claim 6, wherein comparing the tumor as visualized in step (b) to the tumor as visualized in step (d) comprises comparing the size of the tumor visualized in step (b) to the size of the tumor visualized in step (d).

9. The method of claim 4, wherein, when a tumor is present in the subject, the method further comprises administering a cancer treatment to said subject.

10. The method of claim 9, wherein the cancer treatment is selected from surgery, radiation, and chemotherapy.

11. The method of claim 9, wherein the cancer treatment is administered directly to the visualized tumor.

* * * * *

SEQUENCE LISTING

<160> NUMBER OF SEQ ID NOS: 6

<210> SEQ ID NO 1
<211> LENGTH: 59
<212> TYPE: DNA
<213> ORGANISM: Artificial sequence
<220> FEATURE:
<223> OTHER INFORMATION: synthethic sequence -continued

```
<220> FEATURE:
<221> NAME/KEY: misc_feature
<222> LOCATION: (1)..(1)
<223> OTHER INFORMATION: amine

<400> SEQUENCE: 1
catcgccctg gactagcata cccatgaaca caagttgcgt cacgatgaga ctggatgaa      59

<210> SEQ ID NO 2
<211> LENGTH: 40
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: phosphate
<220> FEATURE:
<221> NAME/KEY: misc_feature
<222> LOCATION: (40)..(40)
<223> OTHER INFORMATION: amine

<400> SEQUENCE: 2
tcacggtagc ataaggtgca cgttaccttg attcccgtcc                           40

<210> SEQ ID NO 3
<211> LENGTH: 26
<212> TYPE: DNA
<213> ORGANISM: Artificial sequence
<220> FEATURE:
<223> OTHER INFORMATION: synthetic sequence

<400> SEQUENCE: 3
auagcuaccg ugauucaucc agtgag                                          26

<210> SEQ ID NO 4
<211> LENGTH: 20
<212> TYPE: DNA
<213> ORGANISM: Artificial sequence
<220> FEATURE:
<223> OTHER INFORMATION: synthetic sequence

<400> SEQUENCE: 4
acccatgaac acaagttgcg                                                 20

<210> SEQ ID NO 5
<211> LENGTH: 20
<212> TYPE: DNA
<213> ORGANISM: Artificial sequence
<220> FEATURE:
<223> OTHER INFORMATION: synthetic sequence

<400> SEQUENCE: 5
ggacgggaat caaggtaacg                                                 20

<210> SEQ ID NO 6
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: link to 6-carboyxfluorescein
<220> FEATURE:
<221> NAME/KEY: misc_feature
<222> LOCATION: (9)..(10)
```

```
<223> OTHER INFORMATION: link to internal quencher
<220> FEATURE:
<221> NAME/KEY: misc_feature
<222> LOCATION: (26)..(26)
<223> OTHER INFORMATION: link to Iowa Black forward quencher

<400> SEQUENCE: 6
tggatgaatc acggtagcat aaggtgca                                              28
```